(12) United States Patent
Hansma et al.

(10) Patent No.: US 8,398,568 B2
(45) Date of Patent: *Mar. 19, 2013

(54) METHODS AND INSTRUMENTS FOR ASSESSING BONE FRACTURE RISK

(75) Inventors: Paul K. Hansma, Isla Vista, CA (US);
Douglas J. Rehn, Lompoc, CA (US);
Georg Fantner, Santa Barbara, CA (US); Patricia J. Turner, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/006,974

(22) Filed: Jan. 14, 2011

(65) Prior Publication Data
US 2011/0152724 A1 Jun. 23, 2011

Related U.S. Application Data

(63) Continuation of application No. 11/417,494, filed on May 4, 2006, now Pat. No. 7,878,987.

(60) Provisional application No. 60/678,830, filed on May 5, 2005.

(51) Int. Cl.
*A61B 5/103* (2006.01)
*A61B 5/117* (2006.01)
*G01N 3/48* (2006.01)
*G01N 3/42* (2006.01)
*G01N 3/32* (2006.01)
*G01N 3/44* (2006.01)

(52) U.S. Cl. ............ 600/587; 73/81; 73/82; 73/83

(58) Field of Classification Search ............ 600/587; 73/81, 82, 83, 85
See application file for complete search history.

(56) References Cited

U.S. PATENT DOCUMENTS

| 4,304,123 A | 12/1981 | Aschinger et al. |
| 4,611,487 A | 9/1986 | Krenn et al. |
| 4,799,498 A | 1/1989 | Collier |
| 5,433,215 A | 7/1995 | Athanasiou et al. |
| 5,503,162 A | 4/1996 | Athanasiou et al. |

(Continued)

FOREIGN PATENT DOCUMENTS

| FR | 2391695 A1 | 12/1978 |
| WO | WO 98/08073 A1 | 2/1998 |

(Continued)

OTHER PUBLICATIONS

M. L. Bouxsein, et al., "Digital X-ray Radiogrammetry Predicts Hip, Wrist and Vertebral Fracture Risk in Elderly Women: A Prospective Analysis from the Study of Osteoporotic Fractures," Osteoporos Int, International Osteoporosis Foundation and National Osteoporosis Foundation, p. 358-365, (Jul. 26, 2002).

(Continued)

*Primary Examiner* — Rene Towa
*Assistant Examiner* — Adam Eiseman
(74) *Attorney, Agent, or Firm* — Jeffrey A. McKinney; McKinney Law Group

(57) ABSTRACT

Methods and instruments for assessing bone, for example fracture risk, in a subject in which a test probe is inserted through the skin of the subject so that the test probe contacts the subject's bone and the resistance of the test bone to microscopic fracture by the test probe is determined. Macroscopic bone fracture risk is assessed by measuring the resistance of the bone to microscopic fractures caused by the test probe. The microscopic fractures are so small that they pose negligible health risks. The instrument may also be useful in characterizing other materials, especially if it is necessary to penetrate a layer to get to the material to be characterized.

16 Claims, 15 Drawing Sheets

U.S. PATENT DOCUMENTS

| | | | |
|---|---|---|---|
| 5,701,913 | A | 12/1997 | McPherson et al. |
| 5,766,137 | A | 6/1998 | Omata |
| 5,782,763 | A | 7/1998 | Bianco et al. |
| 5,879,312 | A | 3/1999 | Imoto |
| 5,897,510 | A | 4/1999 | Keller et al. |
| 5,904,658 | A | 5/1999 | Niederauer et al. |
| 5,989,196 | A | 11/1999 | Chu et al. |
| 6,068,604 | A | 5/2000 | Krause et al. |
| 6,213,958 | B1 | 4/2001 | Winder |
| 6,221,019 | B1 | 4/2001 | Kantorovich |
| 6,247,356 | B1 | 6/2001 | Merck, Jr. et al. |
| 6,285,901 | B1 | 9/2001 | Taicher et al. |
| 6,547,565 | B1 | 4/2003 | Dawood et al. |
| 6,585,666 | B2 | 7/2003 | Suh et al. |
| 6,856,834 | B2 | 2/2005 | Treppo et al. |
| 2005/0113691 | A1 | 5/2005 | Liebschner |
| 2006/0184251 | A1 | 8/2006 | Zhang et al. |
| 2007/0191737 | A1 | 8/2007 | Freeman et al. |

FOREIGN PATENT DOCUMENTS

| | | |
|---|---|---|
| WO | WO 99/53292 A1 | 10/1999 |

OTHER PUBLICATIONS

Joint Bone Spine, "Benefits, limitations and impact of osteoporosis risk factor identification," Elsevier SAS, No. 71, p. 361-362, (Jul. 26, 2004).

Robert Marcus et al, "The Nature of Osteoporosis," Academic Press, p. 647-659, (Jul. 26, 1996).

C.H. Turner, "Biomechanics of Bone: Determinants of Skeletal Fragility and Bone Quality," Osteoporosis International, Osteoporos Int. Ed., No. 13, p. 97-104, (Jul. 26, 2002).

Curry, John, "Incompatible mechanical properties in compact bone," Journal of Theoretical Biology 231 (2004) 569-580.

T. Llyra, et al.,"Indentation instrument for the measurement of cartilage stiffness under arthroscopic control," Medical Engineering & Physics, No. 17, p. 395-399, (Jul. 26, 1995).

J. Toyras, et al., "Estimation of the Young's modulus of articular cartilage using an arthroscopic indentation instrument and ultrasonic measurement of tissue thickness," Journal of Biomechanics, Elsevier Science Ltd., No. 34, p. 251-256.

Tiina Lyyra-Laitinen, et al., "Optimization of the arthroscopic indentation instrument for the measurement of thin cartilage stiffness," Phy. Med. Bio, IOP Publishing Ltd., No. 44, p. 2511-2524, (Jul. 26, 1999).

P. A. J. Brama, et al.,"The Application of an Indenter System to Measure Structural Properties of Articular Cartilage in the Horse. Suitability of the Instrument and Correlation with Biochemical Data," J. Vet. Med, Blackwell Wissenschafts-Verlag (Berlin), No. 48, p. 213-221.

Yan-Ping Huang, et al.,"Quasi-linear viscoelastic properties of fibrotic neck tissues obtained from ultrasound indentation tests in vivo," Clinical Biomechanics, Elsevier Ltd., No. 20, p. 145-154, (Jul. 26, 2004).

Yong-Ping Zheng, et al., "An Ultrasound Identation System for Biomechanical Properties Assessment of Soft Tissue In-Vivo," IEEE Transactions of Biomedical Engineering, vol. 43 (No. 9), p. 912-918, (Sep. 26, 1996).

Jyrk J. Parkkinen, et al.,"A Mechanical Apparatus with Microprocessor Controlled stress Profile for Cyclic Compression of Cultured Articular Cartilage Explants," J. Biomechanics, Pergamon press plc, vol. 22 (No. 11), p. 1285-1291, (Jul. 26,1989).

D. O'Gradaigh, et al., "A Prospective study of discordance in diagnosis of osteoporosis using spine and proximal femur bone densitometry," Osteoporos Inc., International Osteoporosis Foundation and National Osteoporosis Foundation, No. 14.

I. Malkin, et al., "Modeling of Age-Related bone loss using cross-sectional data," Animal of Human Biology, Taylor & Francis Ltd., vol. 29 (No. 3), p. 256-270, (Jul. 26, 2002).

C. Glueer, et al., "Comparison of Quantitative Ultrasound and dual-Energy X-Ray absoptiometry for the prediction of Clinical Fractures in Older Women," European Symposium on Calcified Tissues, (Jul. 26, 2003).

J.P.W. Van Den Bergh, et al., "Measuring Skeletal Changes with Calcaneal Ultrasound Imaging in Healthy Children and Adults: The Influence of Size and Location of the region of Interest," Osteoporosis International International Osteoporosis Foundation and National Osteoporosis Foundation, No. 12, p. 970-979, (Jul. 26, 2001).

Geraldine Falgarone, et al., "Discrimination of osteoporotic patients with quantitative ultrasound using imaging or non-imaging device," Joint Bone Spine, Elsevier SAS, No. 71, p. 419-423, (Jul. 26, 2004).

KT Fielding, et al., "Comparison of calcaneus ultrasound and dual x-ray absorptiometry in children at risk f osteopenia," Journal of Clinical Densitometry, (Jul. 26, 2003)

C.A. Formica, et al., "Comparative Assessment of Bone Mineral Measurements Using Dual X-ray Absorptiometry and Peripheral Quantitative Computed Tomography," Osteoporos Int., European Foundation for Osteoporosis and the National Osteoporosis Foundation, No. 8, p. 460-467, (Jul. 26, 1998).

Sigrid Schneider, et al., "Comparative assessment of bone mineral measurements obtained by use of dual-energy x-ray absorptiometry, peripheral quantitative computed tomography, and chemical-physical analyses in femurs of juvenile and adult dogs," AJVR, vol. 65 (No. 7), (Jul. 26, 2004).

S.A. Steel, et al.,"Development and Evaluation of a Phantom for Morphometric X-ray Absorptiometry," Osteoporos Int., International Osteoporosis Foundation and National Osteoporosis foundation, No. 9, p. 38-44, (Jul. 26, 1999).

M. R. Reed, et al., "The use of digital X-ray radiogrammetry and peripheral dual energy X-ray absoptiometry in patients attending fracture clinic after distal forearm fracture," Bone, Elsevier Inc., No. 34, p. 716-719, (Jul. 26, 2004).

Jukka S. Jurvelin, et al. "Comparison of Optical, Needle Probe and Ultrasonic Techniques for the Measurement of Articular Cartilage Thickness," J. Biomechanics, Elsevier Science Ltd., vol. 28 (No. 2), p. 231-235, (Jul. 26, 1995).

METHODS AND INSTRUMENTS FOR ASSESSING BONE FRACTURE RISK

CROSS REFERENCE TO RELATED APPLICATIONS

This application is a continuation of U.S. application Ser. No. 11/417,494, filed on May 4, 2006, now issued as U.S. Pat. No. 7,878,987, and also claims the benefit of U.S. Provisional Application No. 60/678,830 filed May 5, 2005 and which is incorporated herein by reference. The above-noted Applications are incorporated by reference as if set forth fully herein.

BACKGROUND

1. Field of the Invention

The invention relates to novel methods and instruments for evaluating the strength of human and animal bones.

2. Related Art

Recent measurements of materials properties of bone have demonstrated that there is substantial deterioration of these properties with aging. For example, Nalla, Kruzic, Kinney, & Ritchie, have shown that the stress necessary to initiate cracks in the bone, the initiation toughness, decreases by 40% over 6 decades from 40 to 100 years in human bone even without diagnosed bone disease. Even more dramatically, the crack-growth toughness is effectively eliminated over the same age range [1] This recent research extends and supports earlier research that showed a significant deterioration in another materials property, fracture toughness, with age [2-11]. These measurements suggest that deteriorating materials properties of bone due to aging or disease may play a role in bone fracture risk in addition to the well known factors of decrease in bone mineral density and deterioration of micro architecture.

Fracture risk is now commonly assessed by measuring bone mineral density (BMD) through various techniques including dual energy x-ray absorptiometry, quantitative ultrasound and others. These techniques all measure properties of bone without inducing fracture at any length scale. They are generally believed to be incomplete measures of fracture resistance. This is especially true for young, healthy people, such as Army recruits, for whom these conventional measures of bone fracture risk have been found to be ineffective in assessing fracture risk during basic training [12]. Further, it is known that these measurements, though valuable, do not fully characterize fracture risk in elderly patients or in patients with osteoarthritis, osteoporosis or other bone disease.

Osteoporosis is a major public health concern according to the World Health Organization (WHO) [13]. While 50 million women worldwide suffer from the disease, osteoporosis and osteopenia (low bone mass) are frequently associated with increased age, but both diseases affect people in every stage of life, having a huge impact on people in the workforce. The economic burden of osteoporosis is expected to reach $131.5 billion by 2050 [14]. Healthcare costs in the United States currently exceed $15 billion annually for osteoporosis related treatment [15].

Osteopenia and osteoporosis are frequently asymptomatic and diagnosis is often not ascertained until a fracture has occurred or until a low bone mineral density (BMD) has been determined. The most significant complication of osteoporosis is fracture, often induced by trauma of a very low magnitude [16]. For many, a fracture may mean loss of mobility along with life quality and increased risk of mortality. Numerous interventions have been shown to reduce the risk of fracture in this population; however, despite the overwhelming number of patients falling into the fracture risk categories, facilities for evaluations are inadequate and only those evaluated as the highest risk are adequately tested and treated. The vast majority of those at risk are unevaluated, due to costs considerations [17].

Initially, most patients are subjected to assessment instruments that strive to identify those at risk of low bone mineral density OST (Osteoporosis Self Assessment Tool), SCORE (Simple Calculated Osteoporosis Risk Estimation), SOF-SURF (Study of Osteoporotic Fractures) and OSIRIS (Osteoporosis Index of Risk) are representative of these and often are used by practitioners to determine those cases most in need of BMD measurements while simultaneously improving patient awareness of risk factors. Tests are based on body weight, age and several additional factors. While these tests have a high sensitivity (up to 90%) there are many limitations in accuracy specific to each individual [18].

A plethora of diagnostic Instruments are currently in use for assessing fracture risk in patients, focusing on decrease in bone mineral density and deterioration of micro architecture. Dual-energy x-ray absorptiometry (DEXA) has been used to clinically measure these factors. Bone mineral density currently remains the most widely accepted indicator of fracture risk and is also used for true diagnosis of osteoporosis. DEXA is most commonly accepted as the instrument of choice and is used as the main determinant in evaluating risk, but numerous drawbacks and limitations have been observed. Discrepancies between instruments may have a serious effect on the diagnosis and treatment of patients [19]. Additionally, patients with normal BMD may experience fractures while those with low BMD may be at low risk [18]. Criteria are based on World Health Organizations recommendations and T-Scores exhibit discrepancies depending on the assessment sites. While proposals recommended DEXA evaluations of the hip, a higher incidence of greater bone loss in the spine than in the hip 10 years prior to and shortly after menopause has been reported [20]. Improved functions used to evaluate BMD have been recommended to encompass the distinct periodicity of bone development: adolescence, adult stability and reduction with age [21]. BMD results often fail to adequately diagnose children with high fracture risk.

Quantitative Ultrasound (QUS) has been investigated to determine its usefulness as a diagnostic tool for BMD. The equipment is less expensive than DEXA and is radiation free. An osteoporosis and ultrasound study recruited women between the age of 55 and 79. A comparison was done between DEXA and QUS. Results showed good correlation in predicting future incidence of low trauma fractures [22]. While this instrument may be useful for healthy children and postmenopausal women, the high rate of precision errors and large discrepancies in results ascribed to the diametric variations in calcaneus regions bring its usefulness into question [23]. In another study, osteoporotic patients had a lower QUS than controls but there was a large overlap of values [24]. Calcaneus ultrasound may provide a method of assessment for children with osteopenia and with fragility fractures. K. T. Fielding's research indicates results in Z scores similar to those achieved with DEXA but with only a modest correlation [25].

Peripheral quantitative computed tomography (pQCT) has also been studied in hopes of finding a useful tool for establishing bone fracture risk and was found to be less sensitive than DEXA and determined as a poor assessment tool for discriminating those with fractures [26]. In another investigation, pQCT does seem to be a reliable tool for calculating bone Calcium concentrations [27].

Development of morphometric X-ray Absorptiometry was investigated for determining vertebral deformities. High variability in analysis was determined with inter-operator assessment and the precision of analysis declined relative to complexity of the vertebral shape [28].

X-Ray radiogrammetry used routinely in management of patients with distal forearm fractures has been tested as a means of determining BMD and found to be useful in these instances as an alternative to DEXA without requiring further irradiation [29] but is not considered as an alternative to DEXA for alternate diagnoses.

With the exception of pOCT and DEXA, which quantify calcium content as well as BMD, each of these instruments strives to quantify only bone mineral density. While this is a valuable tool in bone strength indication, it overlooks many other aspects of bone that may well be equally important in determining fracture resistance. Tissue quality along with the size, shape and architecture of bone all influence strength and fragility factors [30,31].

Blood tests are sometimes prescribed to evaluate other conditions that influence bone strength. These cover a wide range of activities from alkaline phosphatase and thyroid stimulating hormone to vitamin D and calcium levels. Many of these tests may be beneficial in diagnostics and in determining treatment protocols [32].

In recent years, the value of indentation techniques in the investigation of the mechanical properties of biological materials including bone, dentin and cartilage has been realized [5, 16, 33-42]. Intrinsic toughness characterizes the resistance of mineralized tissues to cracking and fracture. Indentation protocols offer a means to quantify both the toughness and hardness of the biomaterials [1]. Examinations of the dentin-enamel junction of teeth further confirm the value of indentation protocols for understanding crack propagation and fracture mechanics. Using a Vickers indentation instrument, Imbeni et al. were able to characterize how cracks propagate and where crack-arrest barriers appear. Toughness and hardness factors for the enamel, dentin and the interface between the two were quantified [43]. Vickers indentation testing would, however, be difficult on a living patient because of the need to image, at high resolution, the indentations and the cracks that propagate from the corners of the indentations.

Indentation instruments also currently exist that are designed for use under surgical conditions. One such instrument has been designed to measure the stiffness of cartilage through arthroscopic surgical control [44, 45]. Biomechanical property changes in articular cartilage are early indicators of degeneration in the tissues. A reduction in compressive stiffness of articular cartilage is related primarily to the reduction of proteoglycan content and early detection offers possibilities for treatment to arrest the conditions leading to the degenerative process [44]. A similarly designed instrument was used for measurement of structural properties of the cartilage present near the metacarpal bones in Equine species and the results correlated positively with glycosaminoglycan levels in the tissues [46]. An arthroscopic cartilage indenter has been recently used to detect cartilage softening as the early mechanical sign of degradation not yet visible to the eye [47].

Another instrument, the Osteopenetrometer, was designed for in vivo testing of trabecular bone during surgical procedures. This instrument was developed to characterize the mechanical properties of trabecular bone to obtain information relevant to reducing the problem of implant loosening following total knee arthroplasty [48]. The Osteopenetrometer involved penetrations of lengths of order 8 millimeters and widths of order millimeters in diameter at implant sites during surgery. The goal was to have large enough penetrations to average over many trabeculae inside the trabecular bone.

While each of these advances in technology and diagnostic instrumentation produce significant and valuable data toward accurate diagnosis of bone fragility and osteoporosis, they each require skilled technicians. The limitations of available equipment to assess the growing, aging population, and the high expense incurred when diagnostics are available make these tools prohibitive to many patients that are at high risk for fracture. There exists, to our knowledge, no instrument that can clinically measure the material properties of bone relevant to fracture risk in living subjects without surgical exposure of the bone, including removal of the periosteum. The need for an inexpensive diagnostic tool to assess fracture risk within the clinical environment seems clear. While many researchers are still trying to set standards for evaluations of BMD, many also acknowledge its limitations; such as, the uncertainty of applicability to those who have not yet reached their peak bone mass, and the need for adjustments to results based on anatomical location, bone geometry and ethnic background. There is a strong need for a diagnostic instrument with low cost and low labor requirements that can directly determine indications of fracture risk through microcrack inducement, to enable multitudes of "at risk" patients to receive preventative therapy before suffering a fracture.

SUMMARY OF THE INVENTION

The present invention overcomes the foregoing disadvantages by evaluating material properties of the bone through contact with a test probe. In particular embodiments, one can thereby measure the actual resistance of bone to fracture. A novel instrument is provided that assesses macroscopic bone fracture risk by measuring how resistant the bone is to microscopic fractures caused by a test probe inserted through the skin or other soft tissue and periosteum down to the bone. The microscopic fractures are so small that they pose negligible health risks: the volume of damaged bone can be on the order 0.01 cubic millimeter or smaller in current embodiments. The resistance of the bone to these microscopic fractures is a good indication of the resistance of the bone to macroscopic fracture. Thus, bone fracture risk is assessed by creating microscopic fractures in bone. The advantage of such an instrument is that it gives, with a very quick and inexpensive test, information about bone fracture risk that is not available from any existing instrumentation. This new diagnostic information can be used alone or to supplement the results from conventional diagnostics, such as bone mineral density.

Conceptually, the invention provides methods and instrumentation to assess bone fracture risk in a subject, comprising inserting a test probe through the periosteum and/or soft tissue of the subject so that the test probe contacts the subject's bone, and determining the resistance of the test bone to microscopic fracture by the test probe. The subject can be a living person or animal in a clinical setting where the test probe is inserted through overlying skin, or directly through the periosteum during an operation where the periosteum is exposed, or into a cadaver bone through both skin and periosteum or through soft tissue or only the periosteum, depending on the nature of the experiment. Similarly, the instrument could penetrate the endosteum if an interior surface of bone were surgically exposed. The instrument can also measure directly on bone surfaces that have been surgically exposed. The instrument can also measure directly on bone pieces that have been cut out of subjects, whether or not they are still covered with periosteum or endosteum. The test probe is inserted a microscopic distance into the bone to create one or more microscopic fractures in the bone. Bone fracture risk can be assessed by determining the extent of penetration, or it can be assessed by determining the resistance of the bone to penetration of the test probe.

In a preferred embodiment, the method further includes similarly inserting a reference probe so as to contact the subject's bone without the reference probe significantly penetrating the bone, to serve as a reference for determining the extent of insertion of the tip of the test probe. The test probe can be formed as a rod and the reference probe can be in the form of a sheath in which the test probe is disposed, the end of the sheath proximal the test probe tip serving as the reference. The test probe and reference probe can be sharpened asymmetrically to minimize lateral offset between the tip of the test probe and the tip of the reference probe.

In other embodiments, the test probe is sufficiently sturdy to resist deformation when penetrating the bone, while in still other embodiments, the test probe resists deformation when penetrating weak bone but is deformed by healthy bone. High deformation indicates bone that is fracture resistant, low deformation indicating bone that is at risk for fracture. The test probe can contain a stop surface to prevent penetration into the bone beyond a predetermined distance, facilitating quantification of the deformation.

The test probe can be a single use test probe that can be discarded after use by a patient, or by a physician, as can the reference probe. The test probe can be sterilized as can the reference probe. A manufacturer could supply single use combinations consisting of sterilized test probes with sterilized reference probes in a sterile package.

In still other embodiments, rearward motion of the test probe is resisted as the test probe is pulled out of the bone and the extent of resisting force is determined as a measure of resistance of the bone to fracture. Alternatively, or additionally, bone fracture risk is assessed by determining the force needed to insert the test probe into the bone, and a force versus distance parameter can be generated and correlated with fracture risk.

In particular embodiments, a diagnostic instrument for assessing bone fracture risk in a subject is provided, comprising a housing supporting a test probe constructed for insertion through the periosteum on a bone of a subject, whether or not through soft tissue or other overlying skin, for contacting the subject's bone, and means for evaluating a material property of the bone through contact with the test probe. The material property evaluated by the diagnostic instrument is one or more of:

(a) a mechanical property of the bone;
(b) the resistance of the bone to microscopic fracture by the test probe;
(c) a curve of the indentation depth into the bone versus force needed;
(d) indentation of the bone at a fixed force;
(e) indentation of the bone at a fixed impact energy;
(f) hardness of the bone;
(g) the elastic modulus of the bone;
(h) the resistance of the bone to fatigue fracture;
(i) the resistance to penetration of a screw into the bone;
(j) the rotary friction on the bone;
(k) a curve of the indentation depth vs. time after an impact;
(l) a curve of the force vs. time after impact to set distance;
(m) curves of the indentation depth vs. time for repetitive impacts;
(n) curves of the force vs. time for repetitive impacts; or
(o) the response of the bone to a series or combination of the above measurements.

The test probe is inserted a microscopic distance into the bone to create one or more microscopic fractures in the bone to enable the determination of one or more of:

(a) the extent of insertion of the penetrating end of the test probe into the bone;
(b) the resistance of the bone to penetration of the test probe; or
(c) the resistance of the bone to removal of the test probe after it penetrates the bone.

The diagnostic instrument can include a reference probe constructed for insertion through the periosteum, and any overlying skin or other soft tissue, to contact the bone without the reference probe significantly penetrating the bone, to serve as a reference for determining the extent of insertion of the tip of the test probe. The reference probe can be in the form of a sheath in which the test probe is disposed, the end of the reference probe being proximal the test probe tip serving as a reference. The test probe can be formed as a rod with its tip disposed to extend a maximum predetermined distance beyond the end of the reference probe. The test probe, which can be formed of tool steel or stainless steel (with the tip of the test probe formed of the same material as the shaft of the test probe, or of another material such as diamond, silicon carbide, or hardened steel), and the reference probe, which can be formed from a hypodermic needle, can each be tapered asymmetrically whereby to minimize lateral offset between the test probe tip and the reference probe tip, and are sufficiently sharp to penetrate the periosteum of the bone and any overlying skin or other soft tissue.

The diagnostic instrument can apply a fixed force of a first magnitude to the test probe to determine a starting position of the test probe relative to the reference probe, apply a fixed force of a second magnitude to the test probe, measure a change in position of the test probe relative to the reference probe, reduce the fixed force to the first magnitude, and record the change in the position of the test probe relative to the reference probe. The diagnostic instrument can further determine a force versus distance parameter for the inserted test probe by determining the force needed to insert the test probe a predetermined distance into the bone, and/or the distance the test probe inserts into the bone under predetermined force.

For example, the diagnostic instrument can include a load cell connected to the test probe for determining the force needed to insert the test probe said predetermined distance. To generate the force needed to insert the test probe a predetermined distance into the bone, a solenoid can be electromagnetically connected to a mounting pin, with the test probe connected to an end of the mounting pin, for generating the force. One or more springs can be disposed to oppose action of the solenoid.

The diagnostic instrument can include a linear variable inductance transducer having a core connected to the test probe for determining the distance the test probe inserts into the bone under a predetermined force. Other distance sensors can also be used. For current embodiments it is desirable for the distance sensor to have: 1) sensitivity down to roughly 1 micron, 2) range up to about 1 mm and 3) response time preferably a few milliseconds or faster. Distance sensors with these characteristics include optical distance sensors and capacitance sensors.

To insert the test probe, a rotating cam and a follower pin can be included, the cam having a surface operating on the follower pin, one end of the follower pin being in sliding contact with the cam surface, the other end of the follower pin being connected to the test probe. Other mechanisms to insert the test probe with a rotary motor include a motor-driven, ball screw or Acme screw to convert the rotary motion of the motor to linear motion. The Acme screw has the advantage that it can hold a load in a power off situation enabling measurements of force relaxation vs. time after an indentation to fixed depth. For repetitive cycling without reversing the motor direction, rotary to linear motion mechanisms such as piston mechanisms can be used. Other linear motion generators may also be used. For current test probe geometries the linear motion generator should supply forces up to 10 Newtons with a range of motion up to 1 mm. Sharper or smaller diameter test probes could use less force. Measurements of some pre-yield mechanical parameters such as elastic modulus could use much less, force, down to the milliNewton range. A disadvantage, however, of going to much smaller forces and indentation depths is that the properties of a smaller volume of bone is probed. Our tests to date have shown that it is desirable to have enough Volume to average over at least several osteons, which have typical diameters of order 0.2 mm, to reduce scatter in the measured data.

A guide for the test probe and reference probe can be mounted at the lower end of the housing, the guide and the reference probe being formed to removably connect to each other with aligned passageways through which the test probe extends. The reference probe itself can be removably mounted to the guide. For example, the guide can be formed with an externally threaded neck extending from its lower end, the reference probe being formed with an internally threaded opening about its passageway for threadably mounting to the neck of the guide. In a particular embodiment, the test probe is a single use, replaceable probe. In another particular embodiment, the test probe and reference probe are both single use, replaceable probes The combination of test probe and reference probe can be provided as disposable, replaceable and, optionally, sterile, parts, as can the probe guide.

The diagnostic instrument of the present invention is distinct from previous instruments. It is designed to be used without the need to surgically expose the bone surface. The small diameter probe assembly is inserted through the periosteum and any overlying skin or other soft tissue, down to the bone. It is not necessary to expose or visualize the bone surface. It is also distinct from the OsteoSonic™, developed by Liebschner at Rice University, which uses acoustic waves to measure the structural integrity of bone without penetrating the skin with any sort of probe. The diagnostic instrument of the present invention is designed to probe not only pre-yield parameters like elastic modulus, but also post-yield parameters like toughness by actually creating yield in a small probed volume of the bone.

The diagnostic instrument of the present invention can also be operated with an oscillating force in addition to a slowly varying or static force. This can be accomplished, for example, by feeding a solenoid, a moveable coil in a permanent magnetic field such as used for loudspeakers or other devices for converting electrical current to mechanical force with an oscillating current plus a slowly varying current or static current. The resultant oscillating force can be read from a force sensor such as a load cell. The oscillating distance can be read from a distance sensor such as an LVDT. For higher frequency response, a faster distance sensor such as an optical sensor like the MTI-2000 Fotonic sensor can be used. The optical fiber probe of the sensor can be attached to the body of the instrument and can read the distance to a tab which is connected to the test probe. The amplitude or phase of the oscillating distance as a function of frequency and as a function of slowly varying or static force can be explored to increase diagnostic differentiation.

With a solenoid plus spring system for supplying the force there is nonlinearity and hysteresis in the force as a function of current because the force is a function not only of the current, but also of the position of the core in the solenoid. The nonlinearity and hysteresis cause an abrupt increase in force (rise time of order 1 millisecond) just after the force from the current in the solenoid becomes greater than the spring force. This abrupt increase in force creates an impact on the bone. Alternately an impact can be created with a moving coil, attached to the test probe, in permanent magnetic field such as used for loudspeakers. A plot of the distance into the bone that the test probe moves as a result of this impact vs. time is diagnostic. For example, if the current consists of a static current plus a triangle wave of current at frequencies of order 1 Hz and amplitude sufficient to create impacts at the 1 Hz frequency, then the slope of the distance vs. time plot just after the impact has distinguished baked from unbaked bone in some tests. The slope of the distance vs. time plot in the 10s of milliseconds after the impact was significantly less for the unbaked bone: by more than a factor of 5. This indicates that the unbaked bone impeded the repetitive insertion of the probe better than the baked bone in these tests. For this type of measurement it is necessary to use a distance sensor with faster time resolution than a typical LVDT. Hence we used an optical sensor, the MTI-2000 Fotonic sensor, in our tests. Any other fast distance sensors with the required 1) sensitivity, down to roughly 1 micron, 2) range, up to about 1 mm and 3) response time, preferably a few milliseconds or faster, could be used. Other examples of such sensors include optical lever sensors and capacitance sensors.

Finally, we note that the instrument that we describe here could be used to characterize materials other than bone. It could be used to characterize other tissues such as cartilage and skin. It could be used to measure materials properties of metals such as aluminarn alloys and copper alloys, plastics such as polymethylmethaicrylate and Teflon, wood, and ceramics. It has the advantage that it can be used as a hand held instrument to measure materials properties outside of testing labs. For example, it could be used to measure materials properties of aircraft wings to check for fatigue or welds on pipelines to check for embrittlement. Its narrow combination of test probe and reference probe would allow it to measure on surfaces inaccessible to other testing instruments such as durometers. Further, with a sharpened test probe and reference probe it could penetrate soft coatings such as rust or dirt or polymer coatings or corrosion layers or marine organic deposits to measure the properties of the underlying material. It could test pipes buried underground.

Figure 2:
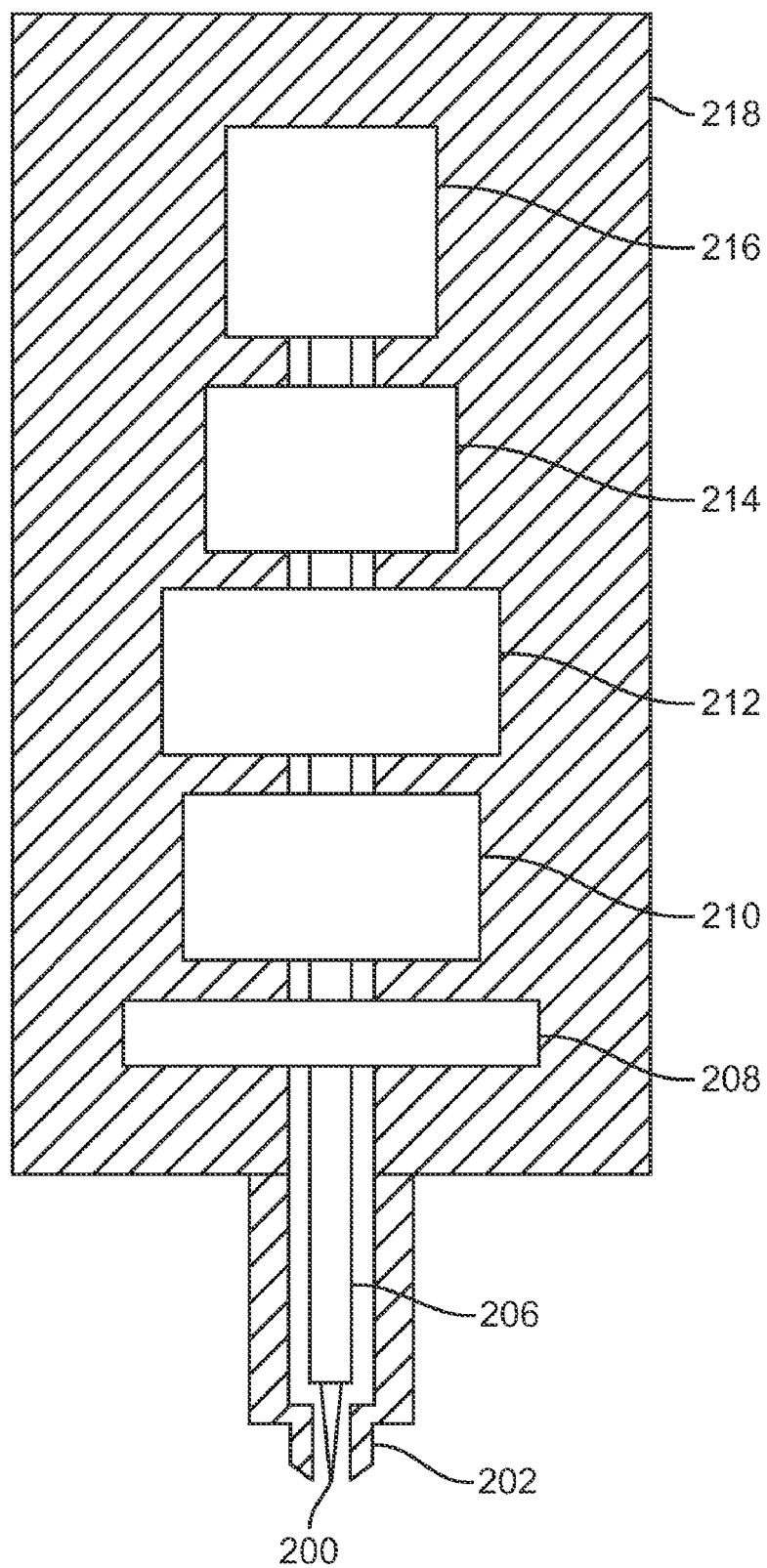
FIG. 2 schematically depicts a generalized diagnostic instrument for a preferred embodiment of the invention.
Figure 5A:
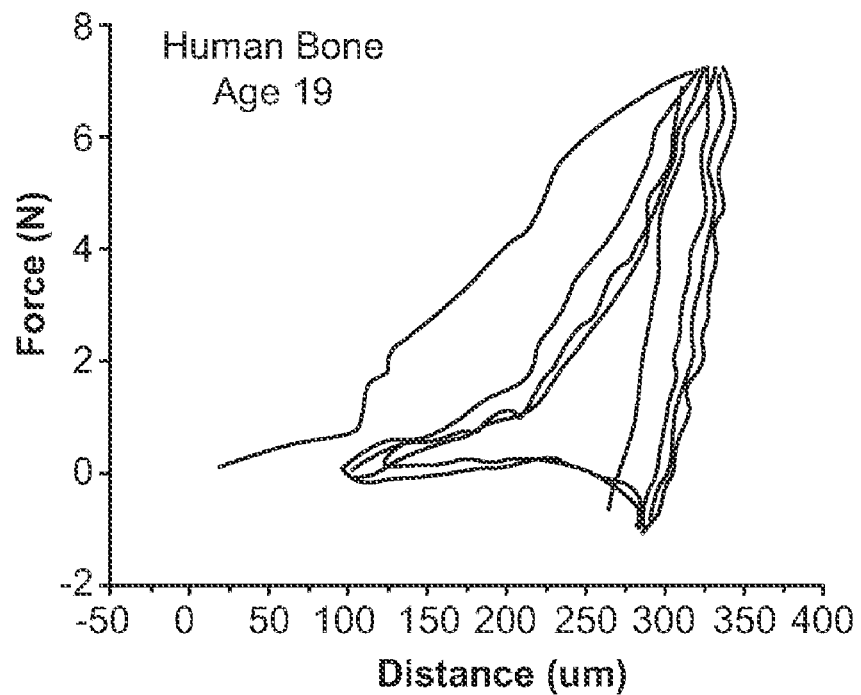
Figure 7:
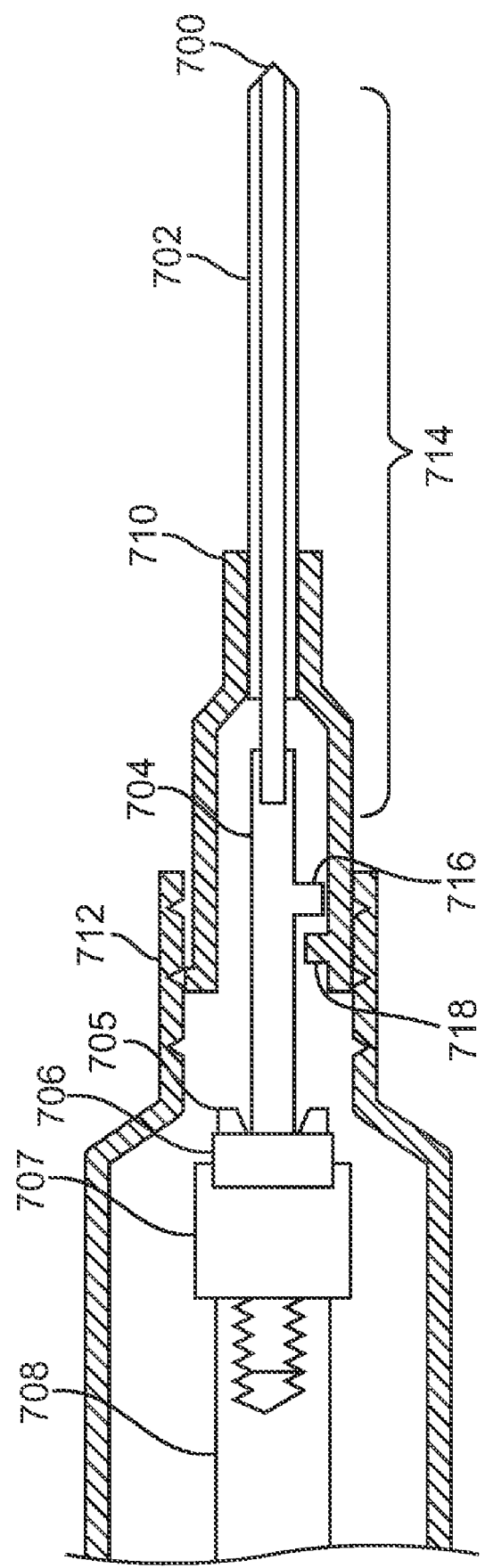
Figure 8:
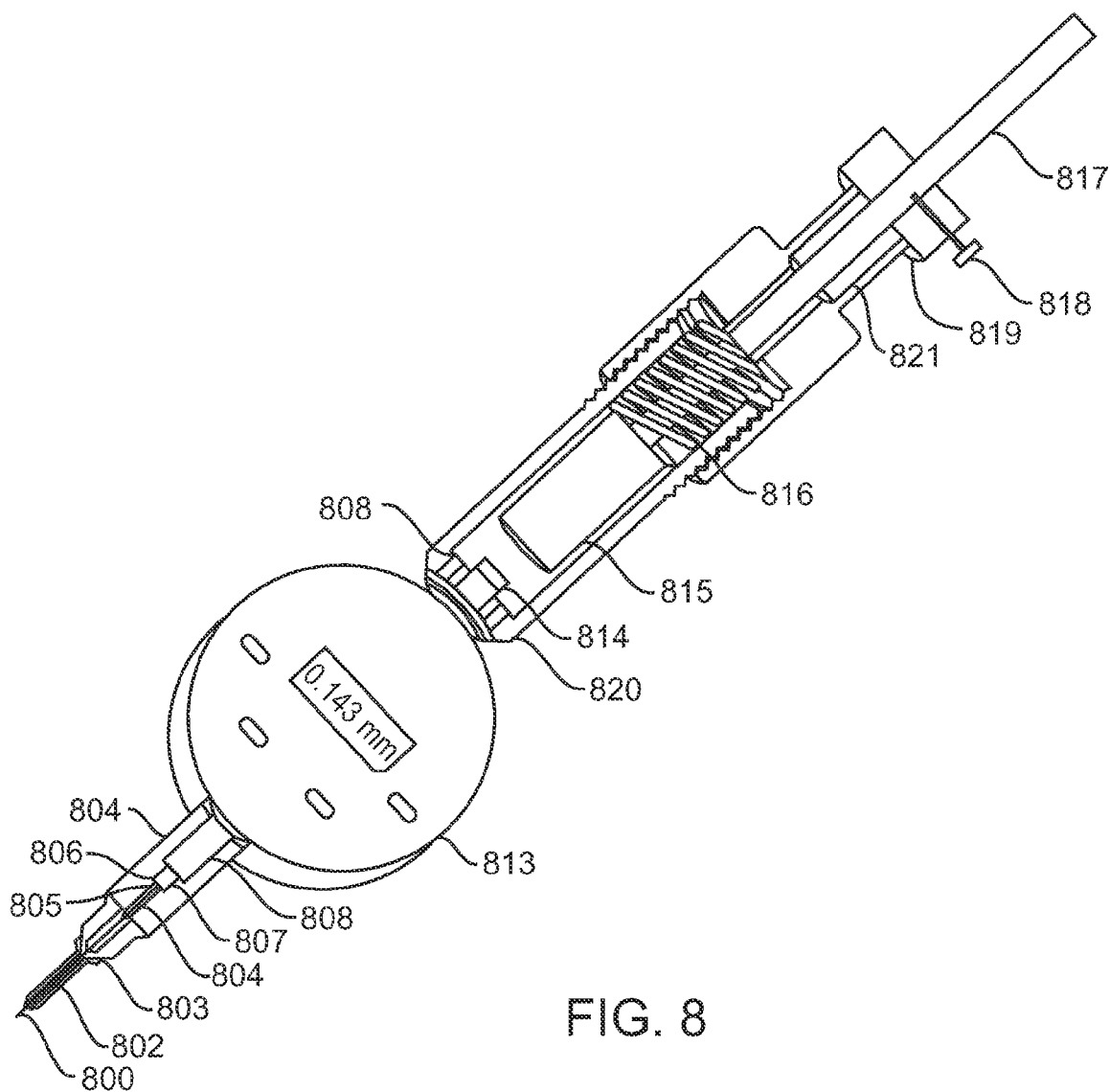
Figure 9A:
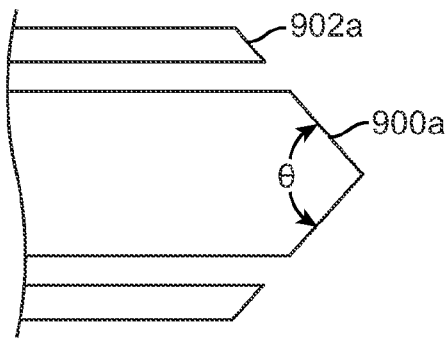
Figure 9B:
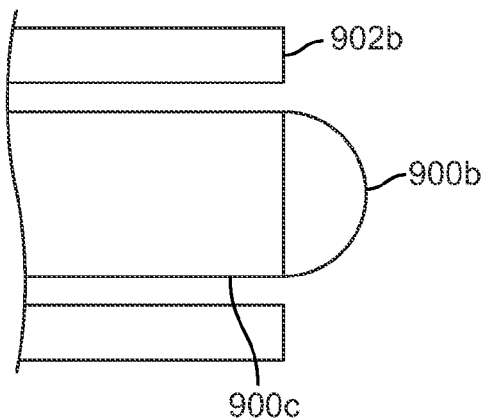
Figure 9C:
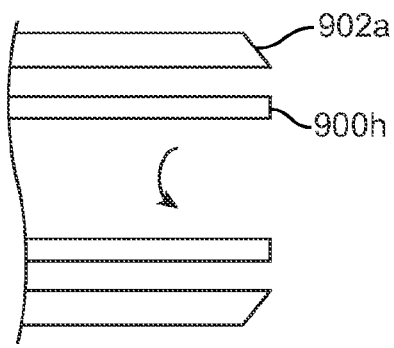
Figure 9D:
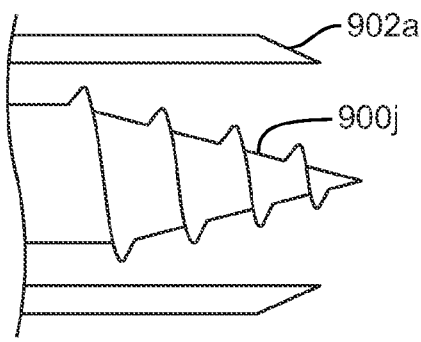
Figure 9E:
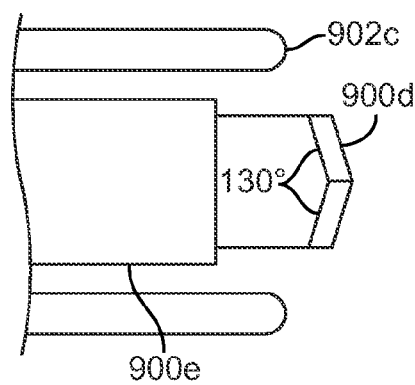
Figure 9F:
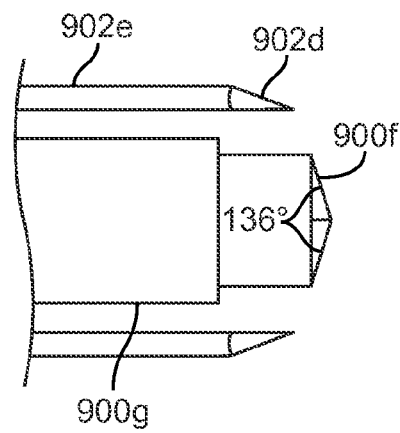
Figure 9G:
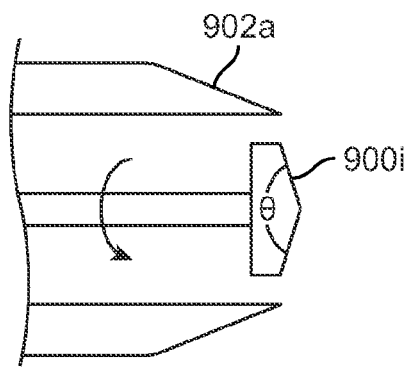
Figure 10A:
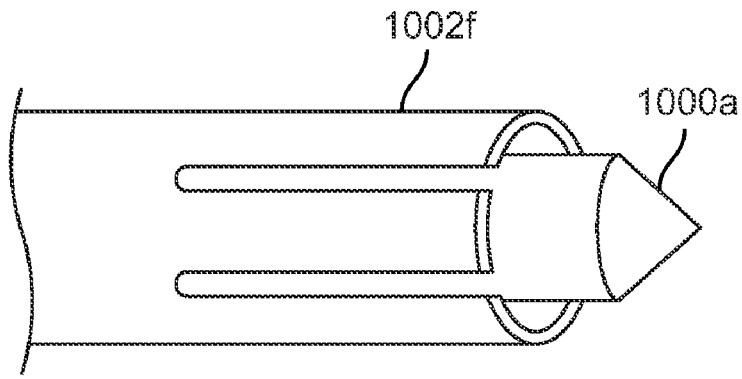
Figure 11:
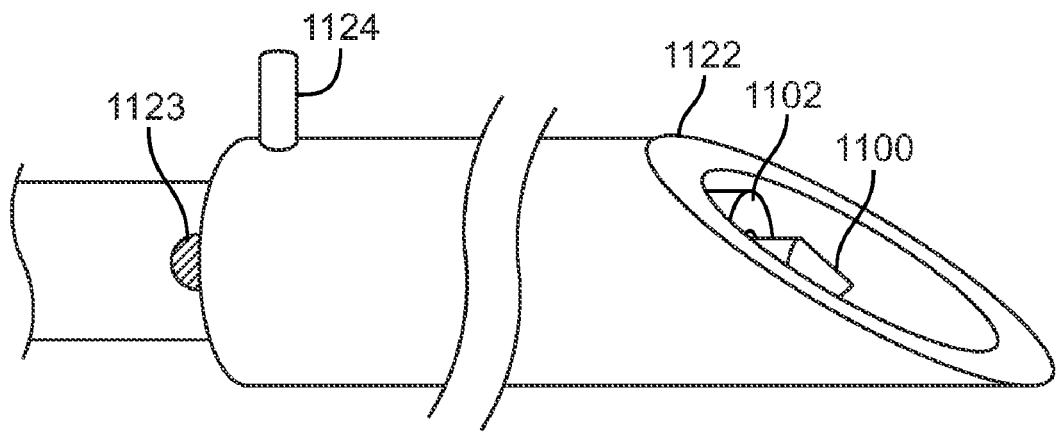
Figure 14:
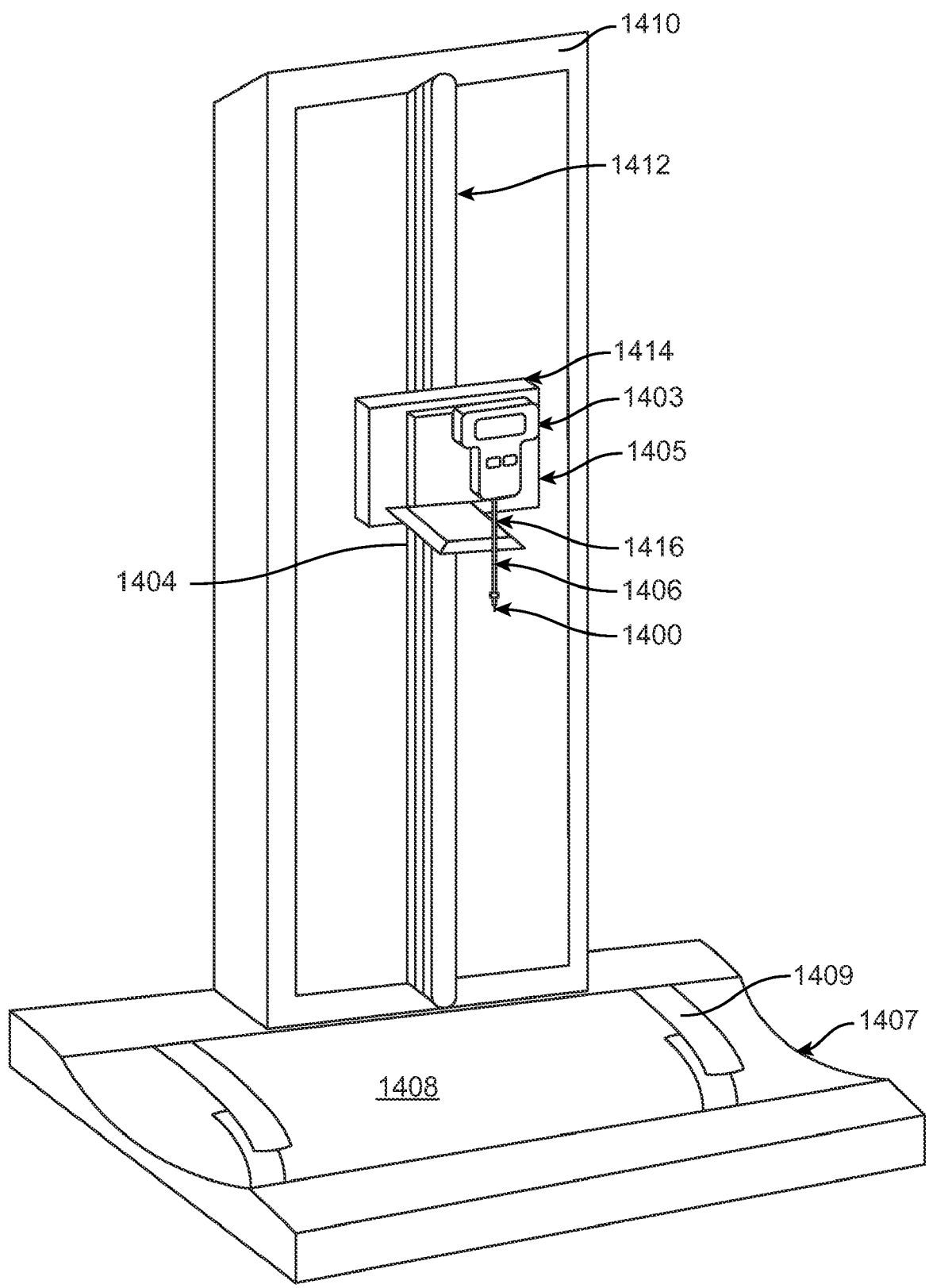
Figure 15:
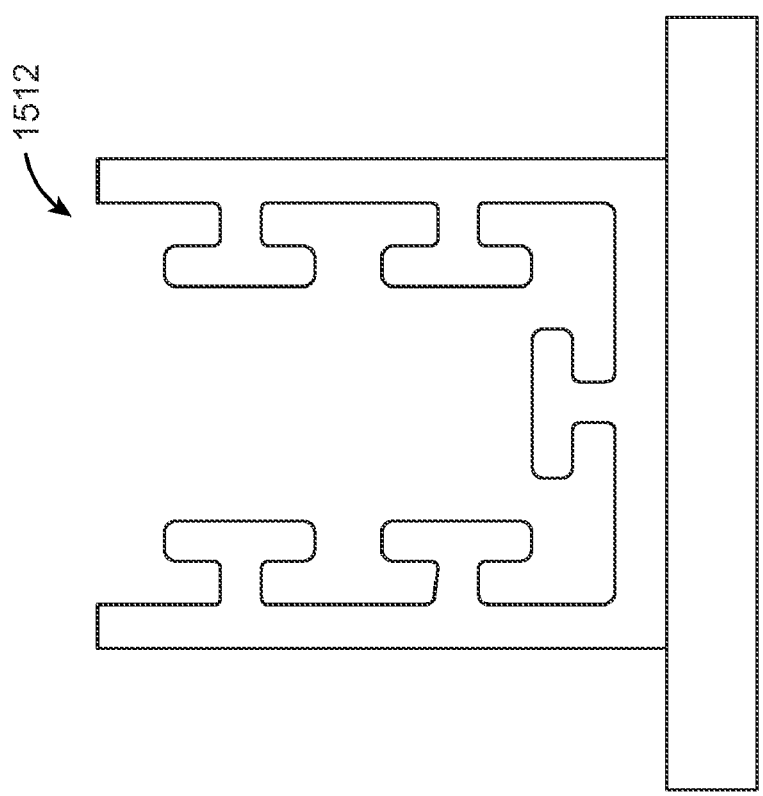
Figure 16:
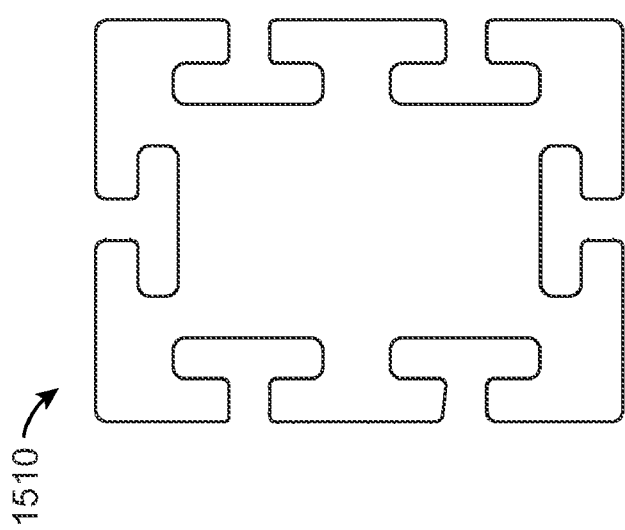
Figure 16:
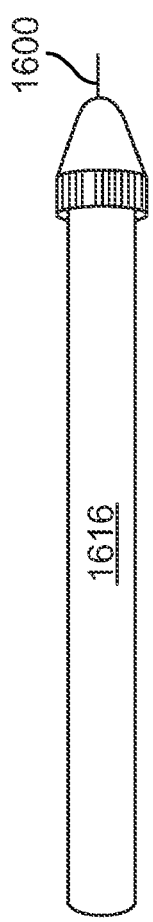
Figure 17:
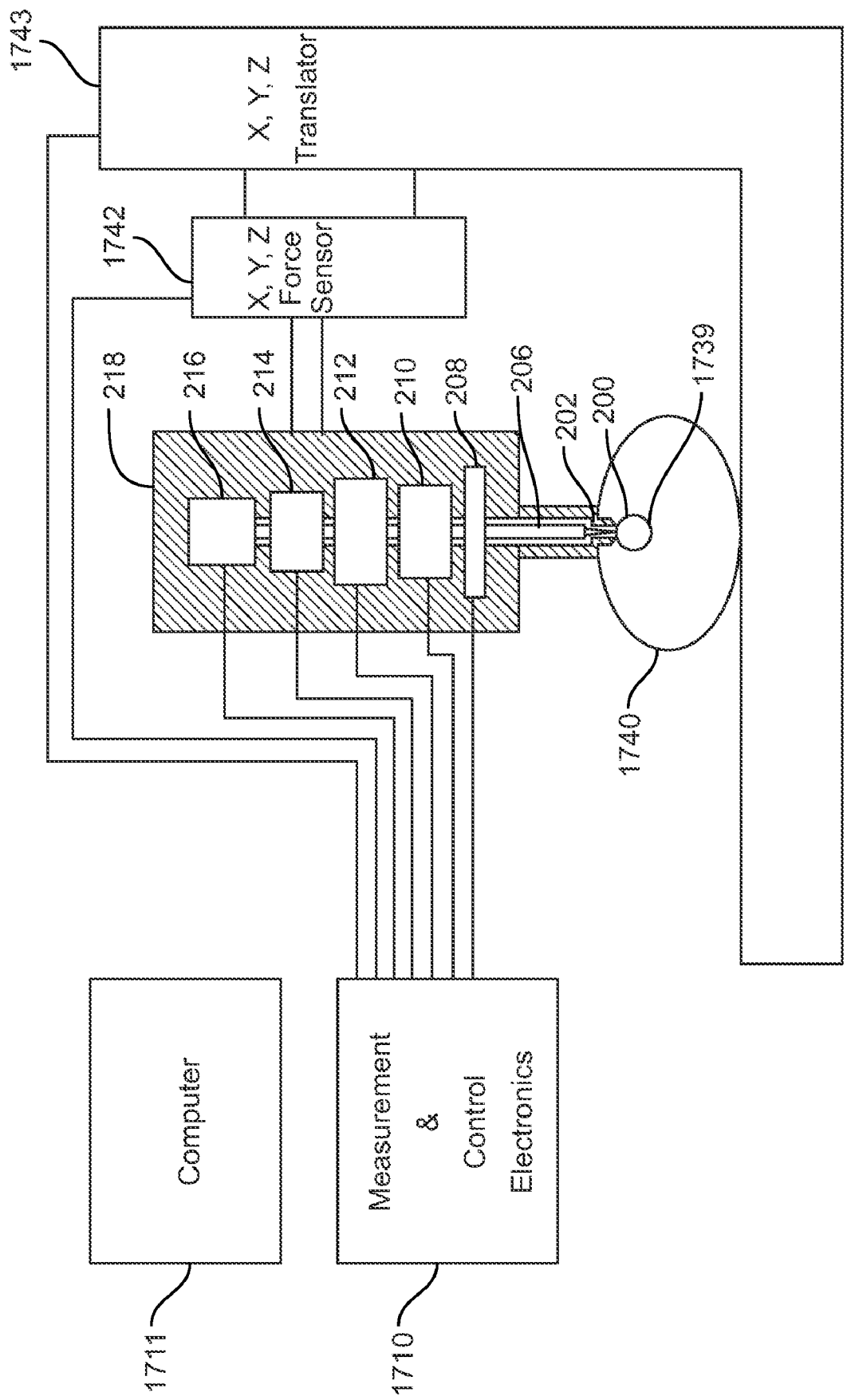

distance versus number of cycles on samples of unbaked and baked bovine bone, all using the diagnostic instrument of FIG. 3;

FIGS. 5a and b depict (a and b) force versus distance curves obtained respectively on samples of age 19 human bone and age 59 human bone, using the diagnostic instrument of FIG. 3;

FIGS. 6a-d depict (a and b) multiple force versus distance curves obtained respectively on samples of baked bovine bone and unbaked bovine bone through soft tissue, and (c and d) force versus number of cycles to a fixed distance obtained again respectively on samples of baked bovine bone and unbaked bovine bone through soft tissue, using the diagnostic instrument of FIG. 3;

FIG. 7 is a cross-sectional view of a combination of a test probe and a reference probe of this invention in accordance with another embodiment;

FIG. 8 is a cross-sectional view of a diagnostic instrument used in an embodiment of FIG. 2;

FIGS. 9a-9g depict the penetrating ends of a variety of test probes that can be used in the invention;

FIGS. 10a and b depict the penetrating ends of other test probes that can be used in the invention;

FIG. 11 depicts the penetrating end of still another test probe that can be used in the invention;

FIGS. 12a-d depict various supports for diagnostic instrument embodiments that can be used in the invention;

FIGS. 13a-d depict embodiments of the force generator that can be used in diagnostic instruments of this invention;

FIG. 14 depicts another embodiment of the invention;

FIG. 15 depicts top views of the slide rail and interconnecting flange used in the embodiment of FIG. 14;

FIG. 16 is a plan view of the test probe vice used in the embodiment of FIG. 14; and FIG. 17 shows electronics used for operation of some diagnostic instruments of FIG. 2.

DETAILED DESCRIPTION OF THE INVENTION

The following will first describe a preferred embodiment, followed by a number of alternative embodiments, all using the underlying principles of the invention.

Preferred Embodiment

Figure 1C:
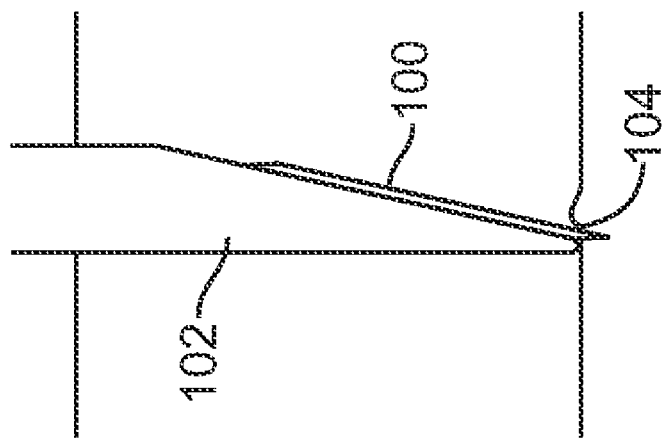
FIGS. 1a, b and c depict an assembly of test probe and reference probe as it is used in three stages of an embodiment of the invention.
Figure 1B:
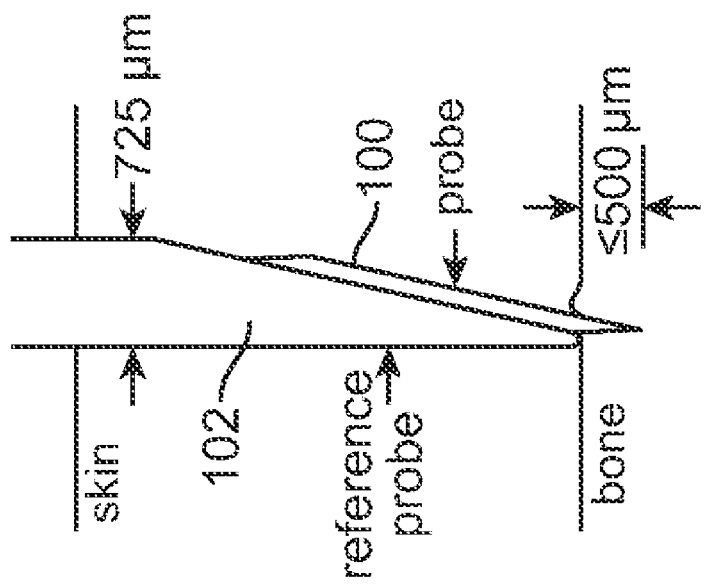
Figure 1A:
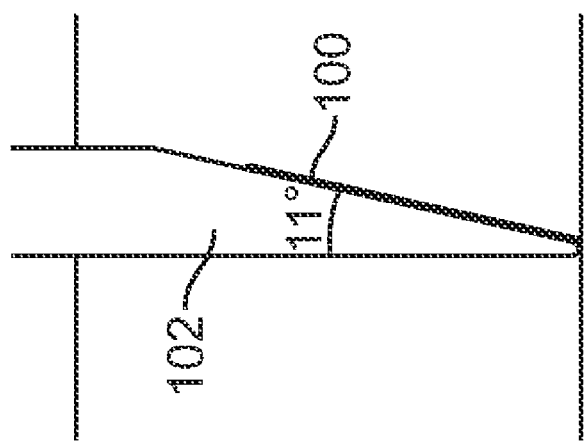

The essential feature of the invention is a test probe, which is inserted through the periosteum and through any overlying skin or other soft tissue to contact a bone surface. Referring to FIGS. 1a-c, the design concept for the diagnostic Instrument of this invention is that a probe assembly, consisting of a test probe 100 and a reference probe 102 is inserted through the periosteum of a bone and any overlying skin or other soft tissue of a living person, animal or cadaver so that it comes to rest on the surface of the bone. Three stages for an exemplary assembly of test probe 100 and reference probe 102 are shown in FIGS. 1a-c. The test probe is inserted into the bone to measure material properties. With a sharpened test probe (for example, sharpened to half angles of order 11 degrees) it is possible to measure post-yield properties and detect irreversible changes in force vs. distance curves. The force vs. distance curves can be processed to give parameters such as: 1) maximum insertion distance, 2) maximum force reached and 3) change of these values after multiple cycles of insertion.

The test probe and reference probe can optionally be sharpened asymmetrically, as shown in FIGS. 1a-c, to minimize the lateral offset between the tip of the test probe 100 and the tip of the reference probe 102. This minimizes the zero offsets in force vs. distance curves that result from bone surfaces that are not completely perpendicular to the axis of the probe assembly. One can alternatively routinely use symmetrically sharpened probes when zero offsets in distance are unimportant, for example, when cycling under a fixed maximum force rather than to a fixed maximum distance, or when sensing the distance at a fixed threshold force and then inserting to a constant distance beyond the distance corresponding to the fixed threshold force. In that case, the test probe 100 can be formed from a rod of tool steel that is 0.5 mm in diameter tipped with a 5 degree to 90 degree cone. It slips inside a #21 syringe, with a specially sharpened end, that acts as the reference probe 102.

An exemplary assembly consists of a sharpened high speed steel rod as the test probe 100 and a sharpened hypodermic needle, 22 gauge as the reference probe 102. FIG. 1 a shows the probe assembly on the surface of the bone just before test probe insertion. Note that the tip of the reference probe 102 has been ground to have its tip close to the tip of the test probe 100.

The distance the test probe 100 is inserted into the bone is measured relative to the position of the reference probe 102 on the surface of the bone. The force to insert and withdraw the test probe 100 is also measured. If the test probe is cycled deeply enough into the bone, typically over a few microns, there will be post-yield damage that can be sampled in subsequent cycles, which is shown in FIG. 1c as a hole 104 remaining in the bone after the test probe is withdrawn.

FIG. 2 shows a generalized diagnostic instrument for the currently preferred embodiment. The test probe 200 is connected through a shaft 206 to an optional torque and angular displacement sensor 208 then to an optional torque generator 210, then to an optional linear displacement sensor 212, then to an optional force sensor 214, and finally to an optional force generator 216. The optional reference probe 202 is connected to the housing 218 that holds the sensors and generators. The housing 218 could be supported and positioned on the sample under test by a support. This does not exhaust the possibilities for measurement or actuation. For example, it is also possible to include an optional linear displacement generator such as shown, by example, in FIG. 3 and used to collect the data in FIG. 6. As another example, a solenoid plus a fixed stop could be used to insert the test probe 200 to a fixed distance. The force vs. time after the insertion would have information about how the bone relaxed after the insertion. In this case the solenoid would generate a force, but as long as the force was larger than needed to insert the test probe 200 to the fixed distance, then it would act like a displacement generator: generating a fixed displacement. This functionality also exists in FIG. 3. Thus the separation between force generator and distance generator is not always clear. Other additions could include a heater to heat the probe that could be wound around the shaft 206.

FIG. 3 shows an enhanced example of the generalized diagnostic instrument shown in FIG. 2. In addition to the components mentioned in FIG. 2, an optional displacement generator 320 consisting of a motor 322, a rotating horizontal cam 324 and a follower pin 326 held in contact with the cam 324 with two springs 328. The motor can be translated laterally with a screw 344 and locked down with screws 346 to adjust the range of motion: the closer the axis of the motor 322 is to the axis of the follower pin 326, the smaller the range of motion. Other embodiments can be constructed without the use of springs. For example, a ball screw or Acme screw can be used to convert the rotary motion of a motor to linear motion. The Acme screw has the advantage that it can hold a load in a power off situation enabling measurements of force relaxation vs. time after an indentation to fixed depth. For repetitive cycling without reversing the motor direction, rotary to linear motion mechanisms such as piston mechanisms can be used. One can sense force with a load cell, Futek model LSB200, acting as the optional force sensor 330, and distance with a linear variable inductance transformer (LVDT), Macro Sensors model CD 375, acting as an optional distance sensor 332. The diagnostic Instrument also has an optional force generator that cycles the test probe 300 into and out of the bone with forces generated by a solenoid 334 in combination with the two springs 328. This combination provides positive forces for insertion, when the force from the solenoid 334 exceeds the force from the two springs 328 and it provides negative forces to pull the test probe out of the bone when the force from the solenoid is less than the force from the two springs. The two adjustable stops 348, which are screws, prevent the solenoid from inserting the test probe too far into the bone. If it is desired to study the response of the bone to forces, then these screws 348 act only as safety devices—they are adjusted to stop the test probe 300 only well beyond the range that is actually probed. Alternately, 1) these screws can be adjusted to give a fixed indentation depth and 2) the current to the solenoid adjusted to be sufficient to insert the test probe 300 all the way until the stops 348 stop the indentation for all samples being tested. Then the response of all the samples to the same indentation can be monitored. In particular embodiments, one can eliminate either the force drive or the distance drive, the instrument operating with just one actuation system. The optional displacement generator 320 consisting of a motor 322, a rotating horizontal cam 324 and a follower pin 326 held in contact with the cam 324 with two springs 328 can also serve another purpose. It can be used to adjust the initial position of the test probe 300 relative to the reference probe 302 for subsequent measurements with a force generator 216 such as the solenoid 334. This adjustment can be made more precise if the motor 322 is a stepping motor, which makes it easier to rotate the cam 324 to a precise position that moves the follower pin 326 and the connected test probe 300 to precisely the desired position relative to the reference probe 302. Alternately, in a diagnostic instrument that will have only an electromagnetic actuation system, the adjustment of the position of the test probe 300 relative to the reference probe 302 can be made with a screw or micrometer that pushes the follower pin 326. This screw or micrometer can be mounted where the motor 322 would have been mounted; it replaces the motor 322 and cam 324.

The force sensor 330 can be any appropriate commercial force sensor, such as an s-beam load cell connected to the follower pin 326 at its top end and to a connector 335 at its bottom end, which in turn is connected to the test probe 300. the LVDT 332 is connected at its top end to the bottom end of the follower pin 326. the bottom end of the LVDT 332 is connected to test probe by a connecting pin 336.

Figures 3A, 3B, 3C:
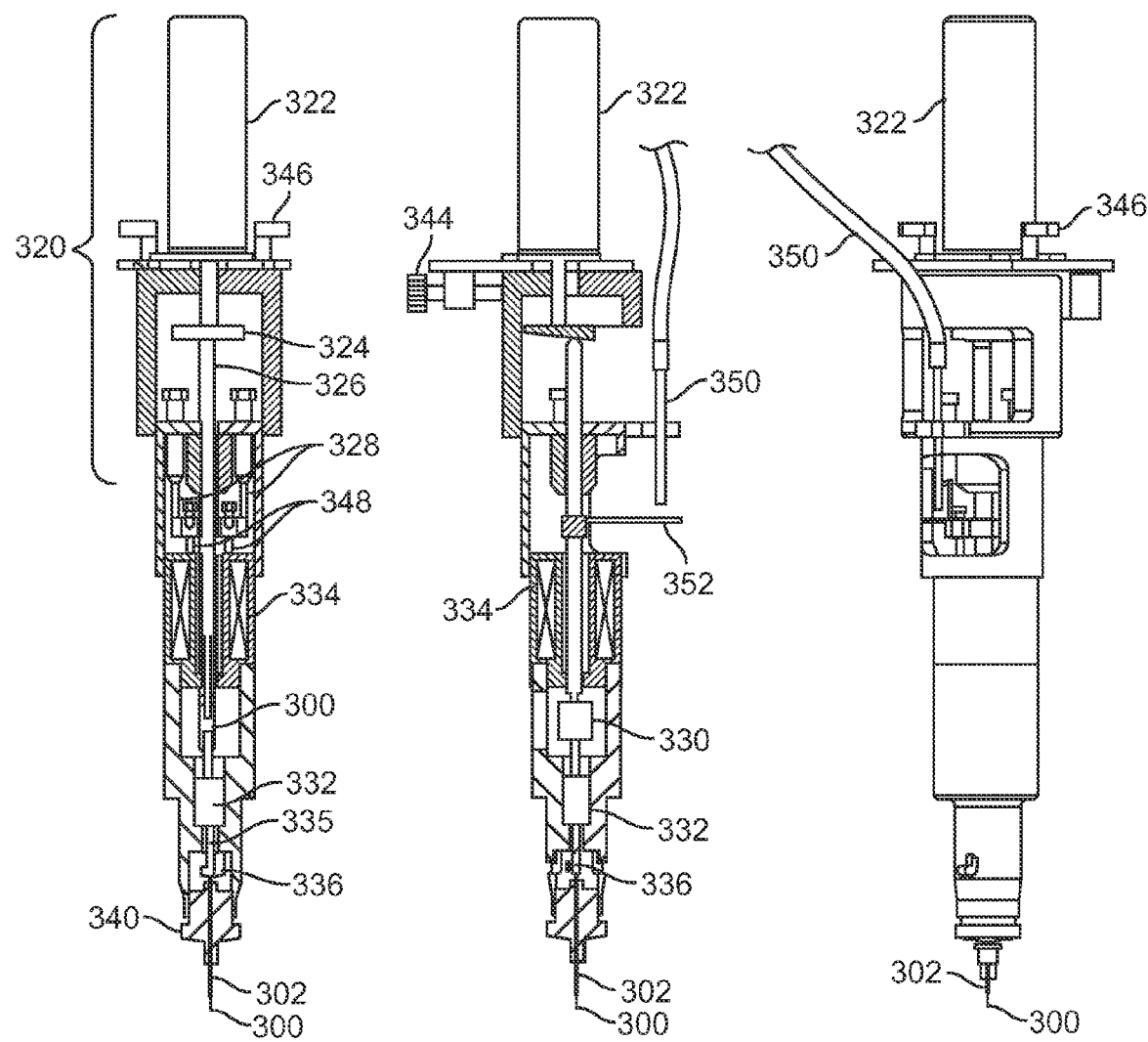
FIGS. 3a, b and c depict respectively front, side and rear views of a specific embodiment of the generalized diagnostic instrument of FIG. 2.
Figure 4A:
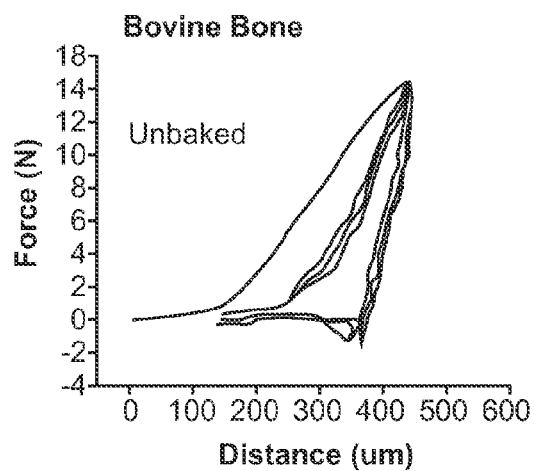
FIGS. 4a-e depict (a and b) force versus distance curves obtained respectively on samples of unbaked and baked bovine bone, (c and d) distance versus time curves respectively on samples of unbaked and baked bovine bone, and (e)
Figure 4B:
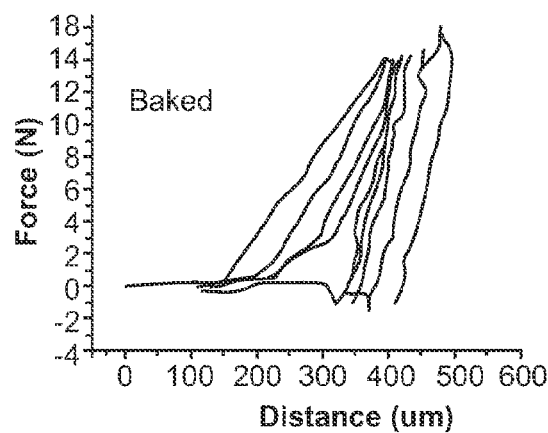
Figure 4C:
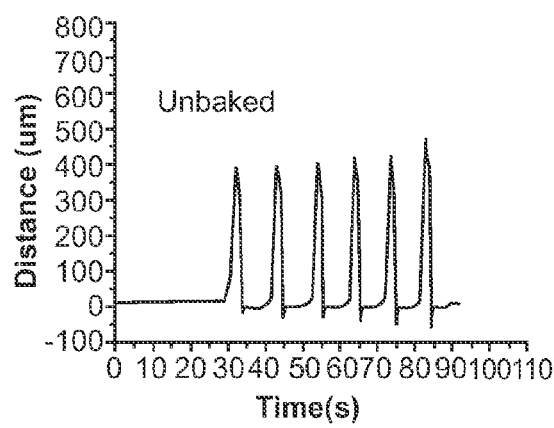
Figure 4D:
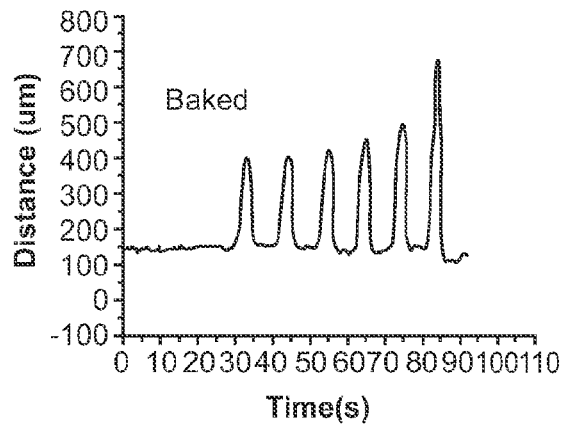
Figure 4E:
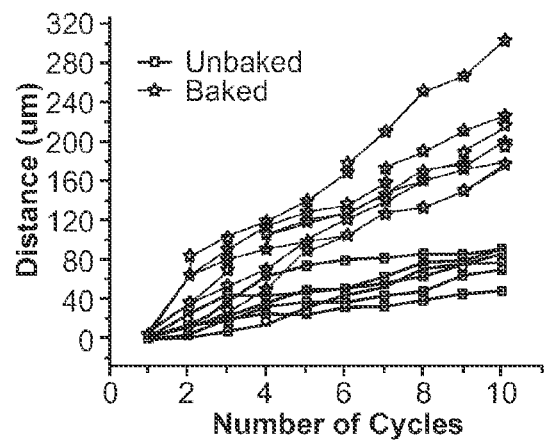

For the embodiment of FIGS. 3a-c, in which the force to pull sharpened test probes 300 out of the bone exceeds 1 Newton, one can clamp the test probe 300 to the connecting pin 336 with a collet 338. The test probe 300 then passes through a guide 340 that can be screwed into and out of the body of the instrument to adjust the projection of the test probe 300 relative to the reference probe 302. The reference probe 302 mounts on a mating neck 342 machined on the end of the guide 340.

The diagnostic Instrument shown in FIG. 3 can be used in two different measurement modes: (1) force controlled or (2) distance controlled. In the first, the test probe gets inserted into the bone until a set force is reached and the measured parameter is the resulting insertion distance. In the second mode, the insertion force is increased until the test probe inserts a set distance. Corresponding to these two modes, the diagnostic Instrument can cycle the test probe into and out of the bone with two different actuation systems. One system, based on a solenoid, is most convenient for cycling to a fixed force. For this a current is supplied to the solenoid by a 0-2 A voltage controlled current source. For operation to a fixed force the current source supplies a current that increases to a fixed maximum. The other system, based on a motor and cam, is most convenient for cycling to fixed distance. As will be shown in the following examples, FIGS. 4 and 5 demonstrate the use of the solenoid system. FIG. 6 demonstrates the use of the motor and cam system.

It is also possible to operate the diagnostic instrument shown in FIG. 3 with an oscillating force in addition to a slowly varying or static force. This can be accomplished, for example, by feeding the solenoid 334 with an oscillating current plus a slowly varying current or static current. The resultant oscillating force can be read from a force sensor 330 such as a load cell 330. The oscillating distance can be read from a distance sensor, 332, such as an LVDT. For higher frequency response, a faster distance sensor such as an optical sensor like the MTI-2000 Fotonic sensor can be used. The optical fiber probe of the sensor 350 can be attached to the body of the instrument and can read the distance to a tab 352 which is connected to the test probe 300. The amplitude or phase of the oscillating distance as a function of frequency and as a function of slowly varying or static force can be explored to increase diagnostic differentiation.

With a solenoid, 1351, plus spring, 1352, system for supplying the force, such as in the embodiment in FIG. 13, there is nonlinearity and hysteresis in the force as a function of current because the force is a function not only of the current, but also of the position of the core in the solenoid. The nonlinearity and hysteresis cause an abrupt increase in force (rise time of order 1 millisecond) just after the force from the current in the solenoid becomes greater than the spring force. This abrupt increase in force creates an impact on the bone. A plot of the distance into the bone that the probe moves as a result of this impact vs. time is diagnostic. For example, if the current consists of a static current plus a triangle wave of current at frequencies of order 1 Hz and amplitude sufficient to create impacts at the 1 Hz frequency, then the slope of the distance vs. time plot just after the impact can easily distinguish baked from unbaked bone. The slope of the distance vs. time plot in the 10s of milliseconds after the impact is significantly less for the unbaked bone: by more than a factor of 5. This indicates that the unbaked bone impedes the repetitive insertion of the probe better than the baked bone. For this type of measurement it is necessary to use a distance sensor with faster time resolution than a typical LVDT. Hence we used an optical sensor, the MTI-2000 Fotonic sensor, in our tests. Any other fast distance sensors with the required 1) sensitivity, down to roughly 1 micron, 2) range, up to about 1 mm and 3) response time, preferably a few milliseconds or faster, could be used. Examples of such sensors include optical lever sensors and capacitance sensors.

Example 1

FIGS. 4a-e show that the diagnostic instrument of this invention can discriminate between baked bovine bone and unbaked, control, bovine bone. This model system of baked vs. unbaked bone is very useful because baking is an easy way to degrade its fracture resistance. Differences in fracture properties become dramatic for bone baked at 250 degrees C. for 2.5 hours [4,49]. The bones are held in a small machinist's vices in a glass bowl that is resting on a simple spring scale on a lab jack. The lab jack is used to raise the scale, bowl, vice and bone until the bone contacts the probe assembly of the diagnostic instrument. The applied preloading force with which the reference probe contacts the bone can be set by continued raising of the lab jack until the desired force is read on the scale. This applied force will set the maximum force that can be used during the testing cycles. If the applied force is exceeded, the reference probe will lift off the bone.

The unbaked, control, bone resists penetration of the test probe better: the distance that the test probe penetrates at fixed force is smaller. The unbaked, control, bone also survives cycling better, i.e. repetitive loading to a fixed force. The maximum penetration that results from each cycle reaches a limit for the unbaked, control bone, while the maximum penetration continues to increase for the baked bone. Note that the maximum force for each cycle increases slightly, especially for the baked bone. This is because we are using open loop electronics that just cycles the current to a fixed maximum. The force from the solenoid is, however, dependent on not only the current, but also on the position of the ferromagnetic core in the solenoid coil. As the distance of penetration increases, the position of the core changes to positions that give slightly more force for the same current. Feedback on the measured force in a closed loop system that controls the current can stabilize the force.

Example 2

FIGS. 5a and b demonstrate that the diagnostic instrument can discriminate between the bone material properties of two individual humans that could be expected, based on previous investigations [1,4,50,51] to have different fracture properties because one is young, 19 years old, and one is elderly, 59 years old. The bone of the younger individual shows increased recovery upon retraction of the probe and requires more force to penetrate repeatedly to the same depth. Further, the maximum penetration distance that results from each cycle reaches a limit for the bone from the younger individual, while the maximum penetration distance continues to increase for the bone from the older individual even though the bone from the younger individual is cycled to a larger fixed force (7 vs. 5.5 Newton). This suggests that the bone from the older individual is less able to resist damage accumulation. Damage accumulation in the form of microcracks has been associated with increased fracture risk [52-55]. Because of the small number of samples, we cannot, however, statistically conclude that that a significant difference has been demonstrated between the bone material properties of bone from younger vs. older individuals.

Example 3

Figure 5B:
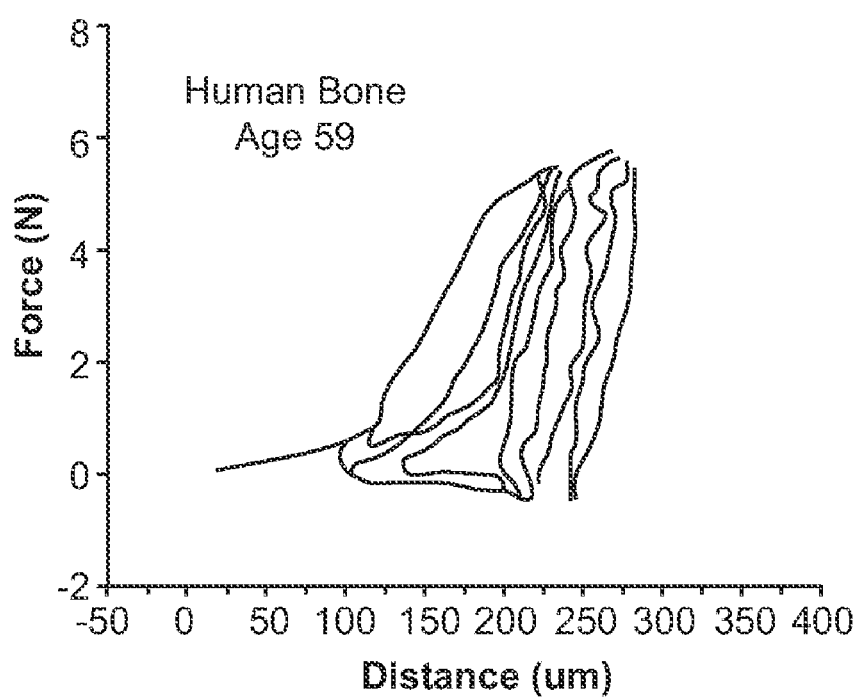
Figure 6A:
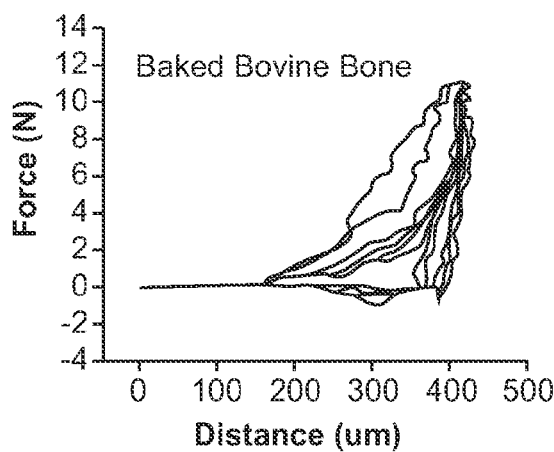
Figure 6B:
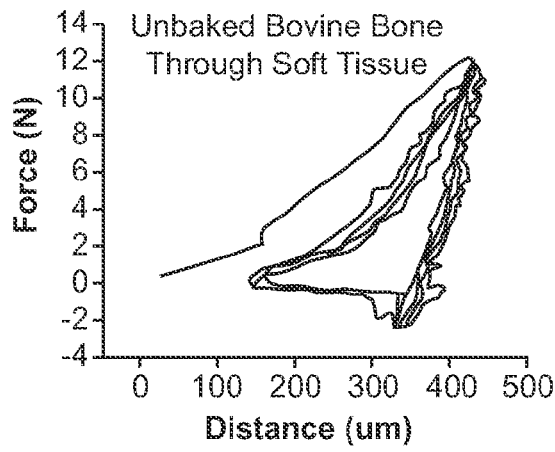
Figure 6C:
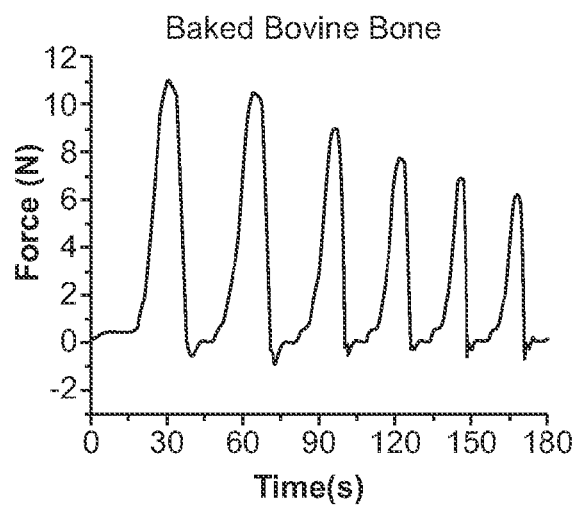
Figure 6D:
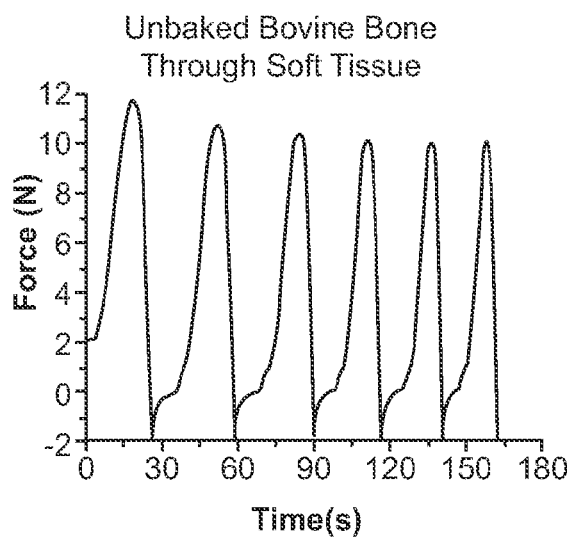

FIGS. 6a-d demonstrate the use of the diagnostic instrument with the alternate actuation system involving a motor and cam rather than the solenoid used in the experiments of FIGS. 4 and 5. In this case the disfance of penetration is controlled with the motor and the force is measured with the load cell. The force necessary to insert the test probe to a fixed distance decreases as the bone is damaged. For unbaked bovine bone, FIGS. 6a-d also demonstrate the ability of the diagnostic instrument to penetrate soft tissue, even the tough periosteum that covers the bone surface, and still make measurements on the bone. Note that the curves of FIG. 6b, measured with the unbaked bone covered with soft tissue, including the periosteum, are very similar to the unbaked bovine curves of FIG. 4, for which all soft tissue, including the periosteum, had been removed from the bone surface.

Alternative Embodiments

In one class of alternative embodiments, small indentations are made into the bone with a sharpened test probe that is sturdy enough to not be deformed by penetrating bone. Examples of this type of test probe include test probes with diamond, silicon carbide, or hardened stainless steel tips. The resistance of the bone to the penetration of this sharpened test probe and/or its response, i.e., resistance, as the sharpened test probe is removed, are indicators of the fracture risk of the bone on the microscopic scale, which are in turn related to the fracture risk of bone on the macroscopic scale.

In different embodiments of the invention, different parameters are measured. For example, in a fully instrumented version, a force vs. distance curve comparable to those taken with existing macro-mechanical testing, nanoindentation, microindentation or AFM indentation equipment is measured, with the sharpened test probe inserted through the skin to contact the bone. In such a version hardness and elastic modulus could be evaluated using the well established protocols and standards that have been established for materials testing with the existing macro-mechanical testing, nanoindentation, microindentation or AFM indentation equipment. Test probe tips for this purpose have been shown in FIG. 9. In some embodiments a sheath over the sharpened test probe comes into contact with the bone surface and serves to define a reference position. The penetration of the sharpened test probe into the bone is then measured relative to the sheath. From measurements of force vs. penetration distance, parameters can be extracted as for conventional indentation testing of materials. In particular, this method can be used to measure recovery properties of bone to repeated indents. This supplies information pertinent to the fatigue resistance of bone, an aspect currently not measured by other devices. A valuable feature of this invention is that it can be done on a living patient with minimal impact and negligible health risks. For pain-sensitive patients, local anesthesia could be injected at the site to be tested.

In other embodiments of the invention, disposable single-use test probes can include good vs. bad indicators and can be available for use by individuals outside a doctor's office to assess their own bone fracture risk. For example, in a specific embodiment of the invention the test probe tip extends a fixed distance beyond a sheath that stops at the bone surface. A spring or elastomer resists the motion of the test probe shaft back into the sheath and an indicator measures the motion of the test probe shaft back into the sheath. As the sheath is pushed until it contacts the bone surface the test probe tip must enter the bone or the test probe shaft must be pushed back into the sheath. The amount that the test probe shaft is pushed back into the sheath is a measure of the resistance of the bone to penetration and fracture; more fracture resistant bone will be indicated by more motion of the test probe shaft back into the sheath rather than penetration of the test probe tip into the bone.

Another embodiment of the instrument uses a special material for a test probe tip that is hard enough to indent weak bone, but not healthy bone. For examples ceramics with controlled porosity or metal alloys or polymers could be used. If such a test probe is inserted to a controlled force—such as in the range of 10 to 1000 milliNewton—then, after it is withdrawn, the deformation of the special material can be quantified: high deformation indicates bone that is fracture resistant; low deformation indicates bone that is at risk for fracture.

Alternatively, the test probe can be inserted up to a stop, for example a broad shoulder on the test probe a fixed distance behind the tip, with the deformation of the special material quantified.

Referring to FIG. 7, a test probe 700 is shown, which passes inside a reference probe 702 and is attached to a mounting pin 704, which passes through an alignment plate 705, and adheres to a magnet 706 mounted in a holder 707 that is screwed into a shaft 708 connected to the diagnostic instrument (FIGS. 8 and 2). The reference probe 702 is mounted in a reference probe holder 710, for example a Luer lock as used in hypodermic needles. The reference probe holder 710 locked onto a mating receptacle 712 connected to the diagnostic instrument.

The probe assembly 714 consisting of the test probe 700, its mounting pin 704, the reference probe 702 and its reference probe holder 710 can be disposable and sterilizable. The probe assembly 714 can be quickly mounted and dismounted from the diagnostic instrument. During mounting, the mounting pin snaps into contact with the magnet 706 as the reference probe holder 710 is mounted onto the mating receptacle 712. An optional test probe stop 716 in combination with a retaining stop 718 can simplify dismounting by pulling the mounting pin 704 off the magnet 706 as the reference probe holder is dismounted. The entire probe assembly 714 then comes off at once, eliminating the need to remove the test probe 700 and its mounting pin 704 separately after the reference probe 702 and the reference probe holder 710 are removed. In this figure, for clarity in this specific example, subcomponents of the probe assembly have been identified with individual numbers. More generally we will use the phrase "combination of test probe and reference probe" to refer to the complete probe assembly ready for mounting on the diagnostic instrument. This combination of the test probe and the reference probe could be supplied sterilized and disposable for single use.

FIG. 8 shows the diagnostic instrument in a preferred embodiment. The test probe 800 is connected via the mounting pin 804, the alignment plate 805, the magnet 806 and the holder 807 to the shaft 808 of a distance sensor 813. In this embodiment, the distance sensor comprises a commercial electronic digital indicator with a range of 0-125 mm and a readout down to 0.001 mm. The position of the test probe is measured relative to the reference probe 802, which is connected via components 803 and 809 to the distance sensor 813.

A force or impact is transmitted through the distance sensor 813 by the shaft 808, which projects above the sensor. In a currently preferred embodiment, an impact plate 814 screwed to the top of the shaft 808 is impacted by a mass 815 that accelerates due to gravitational and/or optional spring 816 forces. The impacts are made reproducible by an indexing shaft 817 which is connected to the mass 815 with an indexing pin 818 that runs through the top cap 819. This top cap is screwed onto the body of the impact device 820 which is, in turn, screwed onto the distance sensor 813. The indexing shaft 817 is kept centered by a linear bearing 821.

The diagnostic instrument in FIG. 8 is a specific example of the more general diagnostic instrument shown in FIG. 2. For the diagnostic instrument in FIG. 8, the optional torque and angular displacement sensor 208 and the optional torque generator 210 are omitted. The optional linear displacement sensor 212 is a digital dial gauge 813. The optional force sensor 214 is omitted. The optional force generator 216 is an assembly of parts 814-820.

Referring to FIG. 9, the test probe 900 and reference probe 902 previously shown in FIG. 7 as 700 and 702 respectively, in FIG. 2 as 200 and 202 respectively and in FIG. 1 as 100 and 102 respectively can have various shapes, and be made of various materials. FIG. 9 shows different possibilities for each. Test probe 900a, designed for testing the fracture resistance of bone, has a cone at its end. In a preferred embodiment $\theta=90$ and the test probe is tool steel. Test probe 900d/c is patterned after the indenters used in some Rockwell and Brinell hardness testing, and has a half sphere of tungsten carbide 900b bonded to a steel shank 900c. Test probe 900d/e is patterned on the diamond indenter used in Knoop hardness testing. It has a pyramid-shaped diamond 900d with apical angles of 130° and about 170°, mounted on a tungsten carbide shank 900e. Test probe 900f/g, has a diamond 900f in the shape of a square-based pyramid whose opposite sides meet at the apex at an angle of 136° as used in Vickers hardness testing of metals and ceramics, mounted on a ceramic shaft 900g. Test probe 900h is a tube that can be rotated for measuring friction on the surface of bone. Test probe 900i is a disk that can be rotated for measuring friction, $\Phi=0$, or viscosity of tissue near a bone surface, at $\Phi=0$ and $\varnothing>0$ as in conventional viscosity measurements. Test probe 900j is a screw that can test bone by measuring the torque necessary to screw it into the bone from inside the reference probe 902a.

Reference probe 902a is designed to penetrate skin and soft tissue before coming to rest on the surface of a bone. Reference probes 902b and 902c are designed for use with an optional outer syringe (FIG. 11) so that they do not need to be sharp for tissue penetration. Reference probe 902d/e is designed for penetrating soft tissue including tough soft tissue on bone surfaces, with the sharpened end 902d that is made of a material such as a soft aluminum alloy or plastic that can penetrate the soft tissue, but flattens when striking the bone and is mounted on a tube of more rigid material such as stainless steel 902e. Other pairings of test probes 900 and reference probes 902 are possible, such as test probe 900b with reference probe 902e/d.

Figure 10B:
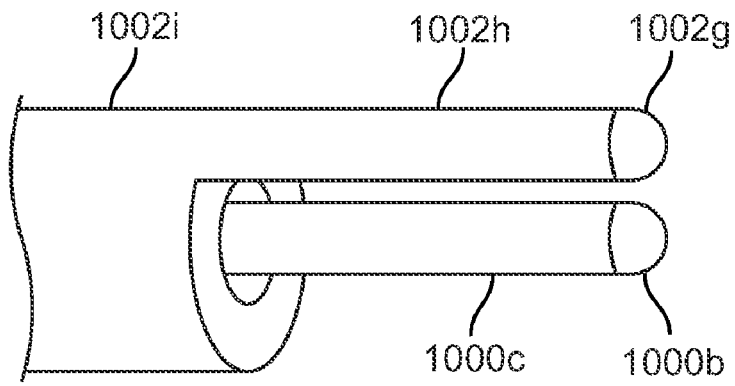

As shown in FIG. 10, reference probes need not be cylindrically symmetric tubes. The reference probe can be a tube with slits 1002f to allow soft tissue to flow out from between the test probe and reference probe. It can be a rod 1002h terminated with ends 1002g. It can also be a hypodermic syringe with optional reground tip as shown in FIG. 1.

As shown in FIG. 11, an optional outer syringe 1122 can be reversibly locked to the reference probe 1102 with an adhesive 1123 such as wax or soft plastic that is designed to stay intact through soft tissue, but break when the outer syringe 1122 hits the bone, thus allowing the test probe 1100 and the reference probe 1102 to contact the bone. Alternately, the outer syringe 1122 can be attached to the reference probe 1102 during insertion by a removable pin 1124. After the removable pin 1124 is removed the reference probe 1102 and test probe 1100 can be slid into contact with the bone to be tested. The outer syringe 1122 can optionally be slid back out of the soft tissue before the bone is tested.

Figure 12A:
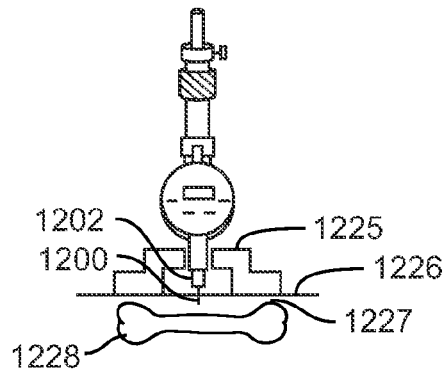

FIGS. 12a-12d show various supports for the diagnostic instrument. In FIG. 12a, the diagnostic instrument slides through a guide 1225 that rests on the skin 1226. The test probe 1201 and reference probe 1202 penetrate the skin 1226 and soft tissue 1227 down to the bone 1228. The guide 1225 keeps the test probe approximately normal to the skin and underlying bone.

Figure 12B:
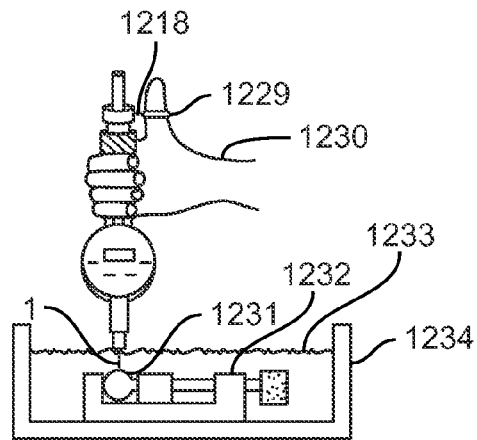

In FIG. 12b, the diagnostic instrument is hand-held. The indexing pin 1218 is pulled out with a thumb ring 1229 to initiate an impact during a test. The bone being tested 1231 is held in a vice 1232 under fluid 1233 contained in a vessel 1234. The diagnostic instrument can also be hand-held used for testing bone in regions of the body when the guide 1225 is not used.

Figure 12C:
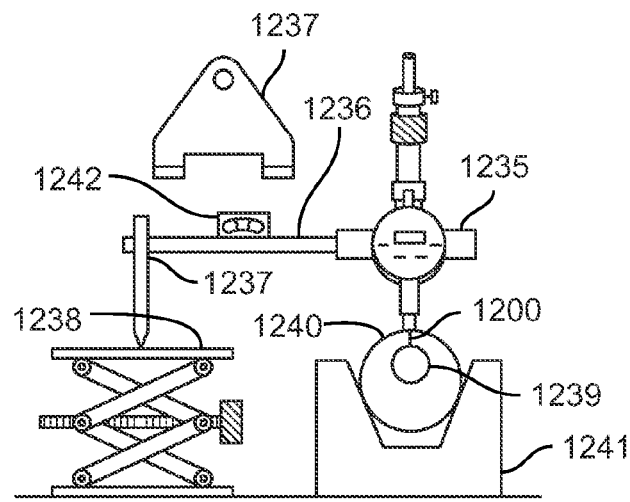

In FIG. 12c, the diagnostic instrument is held in a clamp 1235 that is attached via a rod 1236 to a support plate 1237—as shown rotated 90°—that rests on a lab jack 1238 which can be raised or lowered to adjust for different height samples such as the bone 1239 inside an arm 1240 that rests in a "V" block support 1241. The support plate 1237 moves freely on top of the lab jack 1238 to adjust the lateral position of the test probe. The bubble level 1242 on the rod 1236 guides adjustment of the lab jack 1238 to keep the test probe 1200 vertical.

Figure 12D:
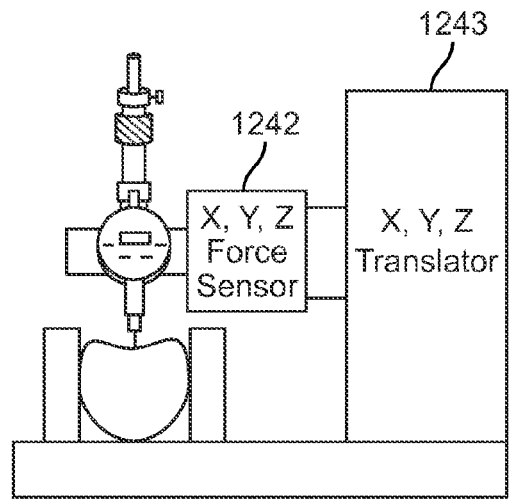

In FIG. 12d, the diagnostic instrument is attached through an x, y, z force sensor 1242 to an x, y, z translator 1243. The translator 1243 controls the lateral positioning of the test probe to directly above the region to be tested and then lowers the test probe at controlled speed. The x, y, z force sensor 1242 can be used to monitor the vertical, z, force during insertion of the test probe and stop the lowering of the test probe by the x, y, z translator 1243 when a given set force is reached. Further, the x, y, z force sensor 1242 can be used in a feedback system to keep the lateral, x and y, forces below set tolerances by positioning the diagnostic instrument with the x and y axes of the x, y, z translator 1243 during insertion of the test probe.

Figure 13A:
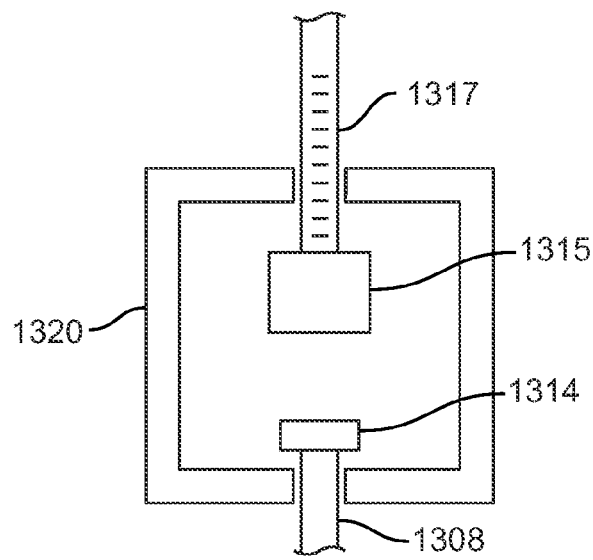

FIGS. 13a-d show various embodiments of the force generator 216 of FIG. 2. FIG. 13a is a schematic version of the force generator shown in FIG. 8 without the optional spring 816 or the indexing pin 818. In operation, the weight 1315 is lifted by shaft 1317 which is graduated so it can be lifted a precise amount. It is dropped, accelerates under gravity, and hits the impact plate 1314 on the shaft 1308.

Figure 13B:
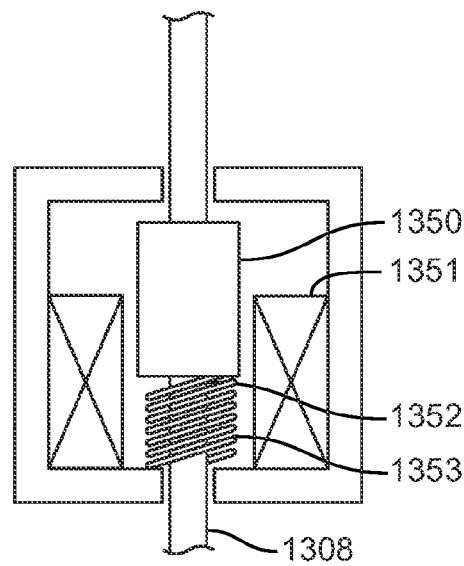

In FIG. 13b, a magnetic core 1350 is pulled down by a coil 1351 to apply a force to shaft 1308. There is an optional gap 1352 between the bottom of the core 1350 and the top of the shaft 1308: for an impact, the gap 1352 is nonzero, allowing the core 1350 to accelerate before impacting the shaft 1308. For a more gradually increasing, steady force, the gap 1352 is zero from the start: the current through the coil 1351 determines the force. A spring 1353 controls the starting position of the core 1350 and returns it to the starting position after an impact or slower varying force is applied by passing current through the coil 1351. This force generator is especially well suited to measurements of the resistance of the bone to fatigue fracture because it is easy to use an electronic pulse generator or other repetitive waveform generator to apply a series of impacts or force cycles to measure the indentation depth as a function of the number of impacts or force cycles.

We have also used this type of force generator for applying a fixed force of a first magnitude to the test probe to determine a starting position of the test probe relative to the reference probe; optionally applying an impact to the test probe; applying a fixed force of a second magnitude to the test probe; measuring the change in position of the test probe relative to the reference probe; reducing the fixed force to the first magnitude; and recording the change in the position of the test probe relative to the reference probe. In this case the force of a first magnitude is applied by a spring that is included inside the distance sensor 813 (FIG. 8) that we used, a Grizzly Digital Indicator, supplemented by an optional external spring (not shown) that surrounds the shaft 807 and, by pushes on a washer (not shown) between the holder 807 and the shaft 808. We have used forces of a first magnitude ranging from 0.1 to 0.8 lbs. We have used forces of a second magnitude ranging from 1 to 3 lbs by applying currents of 0.42 to 1.25 amps to the coil 1351. We used a gap, 1352, of approximately ¼ inch, to supply the impact.

In this case a typical procedure would be:

(1) To zero the instrument by allowing the full weight of the instrument, approximately 4 lbs, to rest on a hard surface so the tip of the test probe 800 is pushed in flush with the end of the reference probe 802 and then zeroing the distance sensor 813.

(2) To insert the test probe 800 and reference probe 802 through the soft tissue down to the bone with the test probe 800 extended approximately 0.02 inches beyond the reference probe 802 and held there by the springs. When the bone is contacted, the test probe 800 is forced back into the reference probe 802 by allowing the full weight of the instrument, approximately 4 lbs. to rest on the bone surface, until the test probe 800 is flush with the end of the reference probe 802 as shown by a reading on the distance sensor 813 of within an acceptable margin of zero (one can generally used an acceptable margin of less than 10 microns). At this time the test probe is applying a force of first magnitude to the bone: we have used 0.8 lbs.

(3) To energize the coil 1351 with a current by using a power supply and a foot switch, we have used a current of 1.25 amps. The reading on the distance sensor is recorded with the current still flowing to the coil 1351.

(4) To stop the current to the coil by releasing the foot switch and taking a second reading. The first reading is a measure of the resistance to penetration by the test probe: 100 microns is typical with smaller values indicating stronger bone. The difference between the first and second reading is a measure of the elastic recovery of the bone: 15 microns is typical with larger values indicating stronger bone.

Figure 13C:
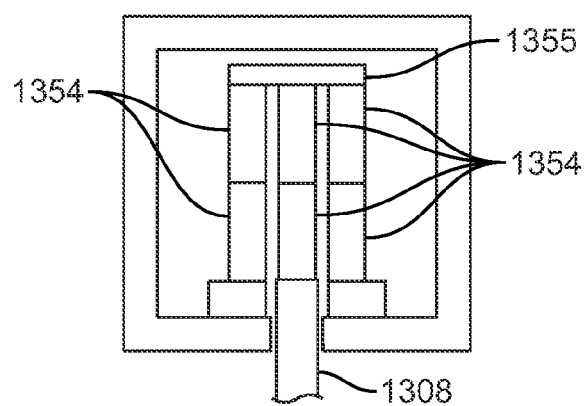

In FIG. 13c, multilayer piezoelectric actuators 1354, such as the Tokin model AE1010D44H40, produce the force. They are shown in a push-pull configuration. To push down on the shaft 1308 the center two are expanded, and the outer four are contracted. They are joined at the top by a coupling plate 1355 which can be glued on with epoxy. In this way, forces up to over 2,000N can be generated with displacements up to 160 µm. These are sufficient for bone indentation experiments with the probe assembly shown in FIG. 7.

Figure 13D:
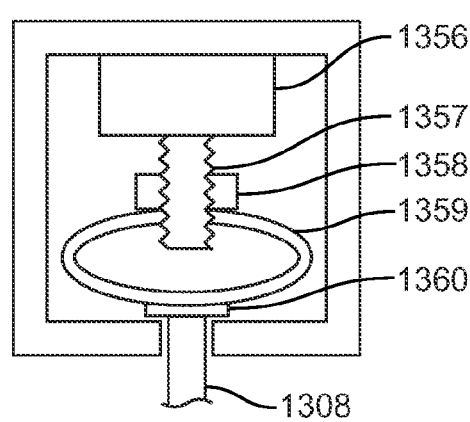

In FIG. 13d, a motor 1356 such as a digital stepper motor, derives a threaded nut 1358 with a rotating screw 1357. This screw can optionally be a ball screw or Acme screw. The Acme screw has the advantage that it can hold a load in a power off situation enabling measurements of force relaxation vs. time after an indentation to fixed depth. This compresses the spring 1359 which is constrained not to rotate. The spring 1359 applies a force to the plate 1360 at the top of the shaft 1308.

An alternate embodiment of the invention is shown in FIG. 14. The frame of the device 1410 is connected to a support stand 1407 for immobilizing the limb of a patient on a firm foam cushion 1408 using Velcro straps 1409.

A slide rail 1412 is attached to the frame. A sliding flange 1414 holds the diagncistic instrument, which in this FIG. 14 consists of a test probe 1400 connected with a test probe vice 1406 via a shaft 1416 to a force and tension gauge 1403. Other examples of diagnostic instruments such as shown in FIGS. 2, 3 and 8 can alternately be mounted on the sliding flange 1414 This assembly of sliding flange 1414 and diagnostic instrument can either: 1) be dropped from a fixed height to deliver an fixed impact or 2) gradually lowered to apply a force approximately equal to the weight of the assembly of sliding flange and diagnostic instrument.

If the assembly of sliding flange 1414 and diagnostic instrument is dropped to deliver an impact then a force and tension gauge 1403 records the force administered at indentation and the tension required to free the test probe 1400 from the bone can both be measured.

If the assembly of sliding flange 1414 and diagnostic instrument is gradually lowered to apply a force approximately equal to the weight of the assembly of sliding flange and diagnostic instrument, then the diagnostic instrument can be operated as discussed above with reference to FIGS. 2, 3 and 8.

In either case, dropping or gradual lowering, the diagnostic instrument can be attached to the sliding flange via a y, 1404, x, 1405 translator that can be used to move the diagnostic instrument laterally to be correctly positioned over the limb of a patient held on a firm foam cushion 1408 using Velcro straps 1409.

FIG. 15 shows a the top view of slide rail 1510 and interconnecting flange 1512.

Referring to FIG. 16, the test probe vice 1616 attaches to directly to the force and tension gauge such as shown in FIG. 14 and has a tightening collar to tighten the jaws that hold the disposable test probe 1600.

FIG. 17 shows the electronics necessary for operation of some diagnostic instruments (FIG. 2). Measurement and control electronics 1710 are needed to read the signals from the optional torque and angular displacement sensor 208, the optional linear displacement sensor 212 and the optional force sensor 214, and to supply signals to drive the optional torque generator 210 and optional force generator 216, as well as the optional x, y, z force sensor 1742 and the optional x, y, z translator 1743. An optional Computer 1711 is needed for implementing complex and/or automated test sequences using programs such as Labview or custom software.

For example, an automated test sequence can include the following steps:

the x, y, z translator 1743 is used under computer 1711 control, to position the test probe 200 above a sample 1739, 1740;

then the diagnostic instrument is lowered until the reference probe 202 penetrates tissue down to the bone 1739 as sensed by an increased z force on the x, y, z force sensor 1742, as measured by the measurement and control electronics 1710;

when a preset value of z force is reached, the computer 1711 stops the x, y, z translator 1743;

then the computer 1711 sends a signal via the measurement and control electronics 1710 to generate a specified force sequence with the force generator 216;

the resultant displacement of the test probe 200 relative to the reference probe 202 is sensed by the linear displacement sensor 212 measured by the measurement and control electronics 1710 and recorded by the computer 1711; and the computer 1711 then sends a signal through the measurement and control electronics 1710 to the x, y, z translator to raise the test probe 200 out of the sample.

As a final example, for a diagnostic instrument to measure the mechanical properties of bone relevant to accepting and holding a screw as used in orthopedic repair, the test probe 200 has a screw shape such as 900*j* in FIG. 9. The optional reference probe is omitted. A torque sensor 208 such as the National Instruments RTS series or the S. Himmelstein MCRT series is used together with a torque generator 210 such as a motor. The displacement sensor 212 is a linear variable differential transducer (LVDT) such as the P3 America model EDCL, or a linear motion potentiometer such as a P3 America model MM10. The force sensor 214 is a load cell such as the National Instruments SLB series or the Sentran ZA series. The force generator 216 is a digital stepper motor driving a spring-screw arrangement as shown in FIG. 13*d*. The entire diagnostic instrument is supported as shown in FIG. 17. The torque needed to screw the test probe 900*j* into the bone is measured by torque and angular displacement sensor 208 for fixed kirce supplied by the force generator 216 as the screw screws into the bone. After the screw is screwed into the bone, the force to pull the screw out is, optionally, measured with the force sensor 216. This same diagnostic instrument could be used with test probe 200 and an optional reference probe 202 to measure the rotary friction of test probe 200 with shape 900*i*, 900*b*, 900*h* or other shapes on the surface of the bone. We have observed that some osteoporotic bone has decreased friction due to fatty deposits on the surface. Thus this rotary friction could be diagnostic for some types of osteoporosis.

REFERENCES

The following publications are hereby incorporated by reference:

1. Nalla, R. K., Kruzic, J. J., Kinney, J. H. & Ritchie, R. O. Effect of aging on the toughness of human cortical bone: evaluation by R-curves. *Bone* 35, 1240-1246 (2004)
2. Bonfield, W., Behiri, J. C. & Charalamides, C. Orientation and age-related dependence of the fracture toughness of cortical bone. in *Biomechanics: Current Interdisiplinary Research* (eds Perren, S. M. & Schneider, E.) (Martinum Nijhoff Publishers, Dordrecht, 1985).
3. Wang, X. D., Masilamani, N. S., Mabrey, J. D., Alder, M. E. & Agrawal, C. M. Changes in the fracture toughness of bone may not be reflected in its mineral density, porosity, and tensile properties. *Bone* 23, 67-72 (1998).
4. Currey, J. D., Brear, K. & Zioupos, P. The effects of ageing and changes in mineral content in degrading the toughness of human femora. *Journal of Biomechanics* 30, 1001-1001 (1997).
5. Rho, J. Y., Kuhn-Spearing, L. & Zioupos, P. Mechanical properties and the hierarchical structure of bone. *Medical Engineering & Physics* 20, 92-102 (1998).
6. Zioupos, P., Currey, J. D. & Hamer, A. J. The role of collagen in the declining mechanical properties of aging human cortical bone. *Journal of Biomedical Materials Research* 45, 108-116 (1999).
7. Brown, C. U., Yeni, Y. N. & Norman, T. L. Fracture toughness is dependent on bone location—A study of the femoral neck, femoral shaft, and the tibial shaft. *Journal of Biomedical Materials Research* 49, 380-389 (2000).
8. Phelps, J. B., Hubbard, G. B., Wang, X. & Agrawal, C. M. Microstructural heterogeneity and the fracture toughness of bone. *Journal of Biomedical Materials Research* 51, 735-741 (2000).
9. Wang, X., Shen, X., Li, X. & Agrawal, C. M. Age-related changes in the collagen network and toughness of bone. *Bone* 31, 1-7 (2002).
10. Wang, X., Li, X., Shen, X. & Agrawal, C. M. Age-related changes of noncalcified collagen in human cortical bone. *Ann Biomed Eng* 31, 1365-1371 (2003).
11. Yeni, Y. N. & Norman, T. L. Fracture toughness of human femoral neck: Effect of microstructure, composition and age. *Bone* 27, 327-327 (2000).
12. Reducing Stress Fracture in Physically Active Military Women (ed. Subcommittee on Body Composition, Nutrition, and Health of Military Women) Academic Press, Washington, 1998.

13. Wehren, L. E. & Sins, E. S. Beyond bone mineral density: can existing clinical risk assessment instruments identify women at increased risk of osteoporosis? *Journal of Internal Medicine* 256, 375-380 (2004).
14. World Health Organization. Collaborating Center *Osteoporosis in the Workplace*. Jean Yves Reginster. March 2005: http://www.osteofound.org/publications/workplace_report.html
15. Ailinger, R. L., Lasus, H. & Braun, M. A. Revision of the facts on osteoporosis quiz. *Nursing Research* 52, 198-201 (2003).
16. Ammann, P. & Rizzoli, R. Bone strength and its determinants. *Osteoporosis International* 14, S13-S18 (2003).
17. Bouxsein, M. L., Palermo, L., Yeung, C. & Black, D. M. Digital X-ray radiogrammetry predicts hip, wrist and vertebral fracture risk in elderly women: A prospective analysis from the study of osteoporotic fractures. *Osteoporosis International* 13, 358-365 (2002).
18. Audran, M. Benefits, limitations, and impact of osteoporosis risk factor identification. *Joint Bone Spine* 71, 361-362 (2004).
19. Formica, C. A. Standardization of BMD measurements. *Osteoporosis International* 8, 1-3 (1998).
20. O'Gradaigh, D., Debiram, I., Love, S., Richards, H. K. & Compston, J. E. A prospective study of discordance in diagnosis of osteoporosis using spine and proximal femur bone densitometry. *Osteoporosis International* 14, 13-18 (2003).
21. Malkin, I., Karasik, D., Livshits, G. & Kobyliansky, E. Modelling of age-related bone loss using cross-sectional data. *Annals of Human Biology* 29, 256-270 (2002).
22. Glueer, C., R. Eastell, D. M. Reid, C. Roux, D. felsenberg, R. Barkmann. Comparison of Quantitative Ultrasound and Dual Energy X-Ray Absorptiometry for the Prediction of Clinical Fractures in Older Women: The OPUS Study $30^{th}$ European Symposium on calcified Tissues—Abstracts (2003).
23. van den Bergh, J. P. W. et al. Measuring skeletal changes with calcaneal ultrasound imaging in healthy children and adults: The influence of size and location of the region of interest. *Osteoporosis International* 12, 970-979 (2001).
24. Falgarone, G. et al. Discrimination of osteoporotic patients with quantitative ultrasound using imaging or non-imaging device. *Joint Bone Spine* 71, 419-423 (2004).
25. Fielding, K. T., Nix, D. A. & Bachrach, L. K. Comparison of calcaneus ultrasound and dual X-ray absorptiometry in children at risk of osteopenia. *Journal of Clinical Densitometry* 6, 7-15 (2003).
26. Formica, C. A., Nieves, J. W., Cosman, F., Garrett, P. & Lindsay, R. Comparative assessment of bone mineral measurements using dual x-ray absorptiometry and peripheral quantitative computed tomography. *Osteoporosis International* 8, 460-467 (1998).
27. Schneider, S. et al. Comparative assessment of bone mineral measurements obtained by use of dual-energy x-ray absorptiometry, peripheral quantitative computed tomography, and chemical-physical analyses in femurs of juvenile and adult dogs. *American Journal of Veterinary Research* 65, 891-900 (2004).
28. Steel, S. A., Thorpe, J. A., Walker, R., Howey, S. & Langton, C. M. Development and evaluation of a phantom for morphometric X-ray absorptiometry. *Osteoporosis International* 9, 38-44 (1999).
29. Reed, M. R., Murray, J. R. D., Abdy, S. E., Francis, R. M. & McCaskie, A. W. The use of digital X-ray radiogrammetry and peripheral dual energy X-ray absorptiometry in patients attending fracture clinic after distal forearm fracture. *Bone* 34, 716-719 (2004).
30. Marcus, R. *Osteoporosis* (ed. Robert Marcus, D. F., Jennifer Kelsey) (Academic Press, London, 1996).
31. Turner, C. H. Biomechanics of bone: Determinants of skeletal fragility and bone quality. *Osteoporosis International* 13, 97-104 (2002).
32. The John Hopkins White Papers, John Hopkins Medical Institution, Baltimore, Md., 40-66 (2004).
33. Rho, J. Y., Tsui, T. Y. & Pharr, G. M. Elastic properties of human cortical and trabecular lamellar bone measured by nanoindentation. *Biomaterials* 18, 1325-1330 (1997).
34. Rief, M., Gautel, M., Oesterhelt, F., Fernandez, J. M. & Gaub, H. E. Reversible unfolding of individual titin immunoglobulin domains by AFM. *Science* 276, 1109-1112 (1997).
35. Hoffler, C. E., Moore, K. E., Kozloff, K., Zysset, P. K. & Goldstein, S. A. Age, gender, and bone lamellae elastic moduli. *Journal of Orthopaedic Research* 18, 432-437 (2000).
36. Hengsberger, S., Kulik, A. & Zysset, P. Nanoindentation discriminates the elastic properties of individual human bone lamellae under dry and physiological conditions. *Bone* 30, 178-184 (2002).
37. Hengsberger, S., Kulik, A. & Zysset, P. A combined atomic force microscopy and nanoindentation technique to investigate the elastic properties of bone structural units. *Eur Cell Mater* 1, 12-7 (2001).
38. Coats, A. M., Zioupos, P. & Aspden, R. M. Material properties of subchondral bone from patients with osteoporosis or osteoarthritis by microindentation testing and electron probe microanalysis. *Calcified Tissue International* 73, 66-71 (2003).
39. Ho, S. P., Balooch, M., Goodis, H. E., Marshall, G. W. & Marshall, S. J. Ultrastructure and nanomechanical properties of cementum dentin junction. *Journal of Biomedical Materials Research Part A* 68A, 343-351 (2004).
40. Silva, M. J., Brodt, M. D., Fan, Z. F. & Rho, J. Y. Nanoindentation and whole-bone bending estimates of material properties in bones from the senescence accelerated mouse SAMP6. *Journal of Biomechanics* 37, 1639-1646 (2004).
41. Balooch, M. et al. Viscoelastic properties of demineralized human dentin measured in water with atomic force microscope (AFM)-based indentation. *Journal of Biomedical Materials Research* 40, 539-544 (1998).
42. Stolz, M. et al. Dynamic elastic modulus of porcine articular cartilage determined at two different levels of tissue organization by indentation-type atomic force microscopy. *Biophysical Journal* 86, 3269-3283 (2004).
43. Imbeni, V., Kruzic, J. J., Marshall, G. W., Marshall, S. J. & Ritchie, R. O. The dentin-enamel junction and the fracture of human teeth. *Nature Materials* 4, 229-232 (2005).
44. Lyyra, T., Jurvelin, J., Pitkanen, P., Vaatainen, U. & Kiviranta, I. Indentation Instrument for the Measurement of Cartilage Stiffness under Arthroscopic Control. *Medical Engineering & Physics* 17, 395-399 (1995).
45. Toyras, J. et al. Estimation of the Young's modulus of articular cartilage using an arthroscopic indentation instrument and ultrasonic measurement of tissue thickness. *Journal of Biomechanics* 34, 251-256 (2001).
46. Brama, P. A. J., Barneveld, A., Karssenberg, D., Van Kampen, G. P. J. & Van Weeren, P. R. The application of an indenter system to measure structural properties of articular cartilage in the horse. Suitability of the instrument and correlation with biochemical data. *Journal of Veterinary Medicine Series a—Physiology Pathology Clinical Medicine* 48, 213-221 (2001).

47. Vasara, A. I., Jurvelin, J. S., Peterson, L. & Kiviranta, I. Arthroscopic cartilage indentation and cartilage lesions of anterior cruciate ligament-deficient knees. *American Journal of Sports Medicine* 33, 408-414 (2005).
48. Hvid, I. Penetration Testing of Bone Using the Osteopenetrometer: (Chapter) Mechanical Testing of Bone and the Bone-Implant Interface, 241-246 (CRC Press, Boca Raton, 2000).
49. Fantner, G. E. et al. Influence of the degradation of the organic matrix on the microscopic fracture behavior of trabecular bone. *Bone* 35, 1013-1022 (2004)
50. Nalla, R. K. EFFECT OF AGING ON THE TOUGHNESS OF HUMAN CORTICAL BONE. *Orthopedic Research Society Proceedings* (2005).
51. Currey, J. D., Brear, K. & Zioupos, P. The effects of aging and changes in mineral content in degrading the toughness of human femora. *Journal of Biomechanics* 29, 257-260 (1996).
52. Vashishth, D., Kim, D. & Rho, J. The influence of tensile and compressive damage on bending fatigue of human cortical bone. in Second Joint EMBS-BMES Conference 2002 24$^{th}$ Annual International Conference of the Engineering in Medicine and Biology Society. Annual Fall Meeting of the Biomedical Engineering Society Vol. 1 417-418 (IEEE, Houston, Tex., 2002).
53. Taylor, D. & Lee, T. C. Microdamage and mechanical behaviour: predicting failure and remodelling in compact bone. Journal of Anatomy 203, 203-211 (2003).
54. Zioupos, P. Accumulation of in-vivo fatigue microdamage and its relation to biomechanical properties in ageing human cortical bone. Journal of Microscopy-Oxford 201, 270-278 (2001).
55. Schaffler, M. B., Choi, K. & Milgrom, C. Aging and matrix microdamage accumulation in human compact bone. *Bone* 17, 521-525 (1995).

The invention claimed is:

1. A method for assessing bone fracture risk in a subject without surgically exposing the bone surface, the method comprising:
    inserting a probe assembly through the skin and soft tissue down to a bone, the probe assembly comprising a reference probe having a tubular section and a test probe slidably disposed within the tubular section;
    establishing a stationary contact point directly on the surface of the bone with the reference probe;
    inserting the test probe a microscopic distance into the bone to create one or more microscopic fractures in the bone; and
    determining one or more of the following parameters:
        the extent of insertion of the penetrating end of the test probe into the bone;
        the resistance of the bone to penetration of the test probe;
        the resistance of bone to removal of the test probe after it penetrates the bone;
    thereby assessing bone fracture risk in the subject.

2. The method according to claim 1, wherein the microscopic fractures are on the order of 0.01 cubic millimeters or smaller.

3. The method according to claim 1, wherein the test probe is a single use test probe, and wherein the test probe is discarded after use.

4. The method according to claim 1, wherein determination of the one or more parameters further comprises determining a distance the test probe inserts into the bone under a predetermined force.

5. The method according to claim 1, wherein the method does not comprise exposing or visualizing the bone surface.

6. The method according to claim 1, wherein the method is applied to a volume of bone allowing the one or more parameters to be determined over at least several osteons.

7. The method according to claim 1, wherein the test probe is symmetrically sharpened.

8. The method according to claim 1, wherein the microscopic fractures are on the order of 0.01 cubic millimeters or smaller, and wherein the test probe is a single use test probe discarded after use, and wherein determination of the one or more parameters further comprises determining a distance the test probe inserts into the bone under a predetermined force, and wherein the method does not comprise exposing or visualizing the bone surface, and wherein the method is applied to a volume of bone allowing the one or more parameters to be determined over at least several osteons.

9. A method for assessing bone fracture risk in a subject without surgically exposing the bone surface, the method comprising:
    inserting a probe assembly through the skin and soft tissue down to a bone, the probe assembly comprising a reference probe having a tubular section and a test probe slidably disposed within the tubular section;
    establishing a stationary contact point directly on the surface of the bone with the reference probe;
    inserting the test probe into the bone to create a yield in a small probed volume of the bone; and
    detecting irreversible changes in force v. distance curves by probing the yield to determine bone toughness,
    thereby assessing bone fracture risk in the subject.

10. The method according to claim 9, wherein the test probe is cycled over a few microns into the bone to create the yield.

11. The method according to claim 9, wherein the test probe is a single use test probe, and wherein the test probe is discarded after use.

12. The method according to claim 9, wherein the force v. distance curves are obtained by determining distances the test probe inserts into the bone under a set of predetermined forces.

13. The method according to claim 9, wherein the method does not comprise exposing or visualizing the bone surface.

14. The method according to claim 9, wherein the method is applied to a volume of bone allowing the force v. distance curves to be determined over at least several osteons.

15. The method according to claim 9, wherein the test probe is symmetrically sharpened.

16. The method according to claim 9, wherein the test probe is cycled over a few microns into the bone to create the yield, and wherein the test probe is a single use test probe discarded after use, and wherein the force v. distance curves are obtained by determining distances the test probe inserts into the bone under a set of predetermined forces, and wherein the method does not comprise exposing or visualizing the bone surface, wherein the method is applied to a volume of bone allowing the force v. distance curves to be determined over at least several osteons, and wherein the test probe is symmetrically sharpened.

* * * * *